United States Patent
Mahanthappa

(10) Patent No.: US 6,767,888 B1
(45) Date of Patent: Jul. 27, 2004

(54) NEUROPROTECTIVE METHODS AND REAGENTS

(75) Inventor: Nagesh K. Mahanthappa, Cambridge, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/418,221

(22) Filed: Oct. 14, 1999

Related U.S. Application Data

(63) Continuation-in-part of application No. 08/883,656, filed on Jun. 27, 1997, now abandoned.

(51) Int. Cl.[7] .................. A61K 38/00; C07K 14/00; C07K 16/00; C07K 17/00
(52) U.S. Cl. .................... 514/2; 514/279; 514/309; 514/312; 530/350; 536/23.1; 436/501
(58) Field of Search ............................. 514/312, 279, 514/309, 2, 317; 530/350; 436/501

(56) References Cited

U.S. PATENT DOCUMENTS

| | | | |
|---|---|---|---|
| 4,456,687 A | 6/1984 | Green | 435/241 |
| 5,223,408 A | 6/1993 | Goeddel et al. | 435/69.3 |
| 5,519,035 A | 5/1996 | Maiese et al. | 514/309 |
| 5,585,087 A | 12/1996 | Lustig et al. | 424/9.2 |
| 5,643,915 A | 7/1997 | Andrulis, Jr. et al. | 514/279 |
| 5,747,507 A | 5/1998 | Ikegaki et al. | 514/312 |
| 5,759,811 A | 6/1998 | Epstein et al. | 435/69.1 |
| 5,789,543 A * | 8/1998 | Ingham et al. | |
| 5,837,538 A | 11/1998 | Scott et al. | 435/325 |
| 5,844,079 A | 12/1998 | Ingham et al. | 530/350 |

FOREIGN PATENT DOCUMENTS

| | | | |
|---|---|---|---|
| EP | 0187 371 A2 | 7/1986 | |
| EP | 0249 873 A2 | 6/1987 | |
| EP | 0874048 A2 | 10/1998 | C12N/15/12 |
| EP | 0879888 A2 | 11/1998 | C12N/15/12 |
| JP | 63 08 81 12 | 4/1988 | |
| JP | 02 27 36 10 | 11/1990 | |
| JP | 04 30 55 28 | 10/1992 | |
| WO | WO 90/02809 | 3/1990 | C12P/21/00 |
| WO | WO 92/15679 | 9/1992 | C12N/15/10 |
| WO | WO 94/28016 | 12/1994 | C07K/13/00 |
| WO | WO 95/18856 | 7/1995 | C12N/15/12 |
| WO | WO 95/23223 | 8/1995 | C12N/15/00 |
| WO | WO 96/09806 | 4/1996 | |
| WO | WO 96/11260 | 4/1996 | C12N/5/00 |
| WO | WO 96/16668 | 6/1996 | A61K/38/17 |
| WO | WO 96/17924 | 6/1996 | |
| WO | WO 97/11095 | 3/1997 | C07K/14/475 |
| WO | WO 97/45541 | 12/1997 | C12N/15/12 |
| WO | WO 98/12326 | 3/1998 | C12N/15/12 |
| WO | WO 98/14475 | 4/1998 | C07K/14/47 |
| WO | WO 98/21227 | 5/1998 | C07H/21/04 |
| WO | WO 98/30234 | 7/1998 | A61K/38/18 |
| WO | WO 98/30576 | 7/1998 | C07K/1/100 |
| WO | WO 98/35020 | 8/1998 | C12N/5/00 |
| WO | WO 99/00117 | 1/1999 | A61K/31/00 |
| WO | WO 99/00403 | 1/1999 | C07H/21/02 |
| WO | WO 99/01468 | 1/1999 | |
| WO | WO 99/04775 | 2/1999 | A61K/31/00 |
| WO | WO 99/10004 | 3/1999 | A61K/38/00 |

OTHER PUBLICATIONS

Foye et al., Chapter 3–5: "Biopharmaceutical Properties of Drug Substances", "Structural Features and Pharmacologic Activity", and "Theoretic Aspects of Drug Design", Principles of Medicinal Chemistry, Baltimore: Williams & Wilkins, Copyright 1995, pages.*

Hsu, CY, Stroke 27(12)2298, 1996.*

Engber et al., Soc. Neurosci. Abs. 26(1–2)Abs No. 792.14, 2000.*

Bowie et al., 1990, Science 247:1306–1310.*

Anderson, R. et al., "Maintenance of ZPA signaling of cultured mouse limb bud cells", Devel. 117:1421–1433 (1993).

Angier, N., "Biologists find key genes that shape patterning of embryos", New York Times, Jan. 11, 1994, C–1.

Basier, K. and G. Struhl, "Compartment boundaries and the control of Drosophila limb pattern by Hedgehog protein", Nature 368:208–214 (1994).

Basler, K. et al., "Control of cell pattern in the neural tube: Regulation of cell differentiation by dorsalin–1, a novel TGFβ family member", Cell 73:687–702 (1993).

Bass, S. et al., "Hormone phage: An enrichment method for variant proteins with altered binding properties",PROTEINS: Structure, Function, and Genetics 8:309–314 (1990).

Bejsovec, A. and E. Wieschaus, "Segment polarity gene interactions modulate epidermal patterning in Drosophila embryos", Development 119:501–517 (1993).

Bienz, M., "Homeotic genes and positional signalling in the Drosophila viscera", TIG 10:22–26 (Jan. 1994).

Bitgood, M. and A. McMahon, "Hedgehog and Bmp genes are coexpressed at many diverse sites of cell–cell cnteraction in the mouse embryo", Dev. Biol. 172(1):126–138 (1995).

Blair, S. S., "Hedghog digs up an old friend", Nature, 373:656–657 (Feb. 23, 1995).

Brand–Saberi, B. et al., "The ventralizing effect of the notochord on somite differentiation in chick embyros",Anat. Embryol. 188:239–245 (1993).

Brockes, J., "We may not have a morphogen", Nature 350:15 (1991).

Bumcrot, D. A. et al., "Proteolytic processing yields two secreted forms of sonic hedgehog", Mol. Cell. Biol. 15(4):2294–2303 (Apr. 1995).

(List continued on next page.)

Primary Examiner—Yvonne Eyler
Assistant Examiner—Michael Brannock
(74) Attorney, Agent, or Firm—Ropes & Gray LLP

(57) ABSTRACT

One aspect of the present application relates to a method for limiting damage to neuronal cells by ischemic or epoxic conditions, e.g., such as may be manifest by a reduction in brain infarct volume, by administering to an individual a hedgehog therapeutic or ptc therapeutic in an amount effective for reducing cerebral infarct volume.

8 Claims, 1 Drawing Sheet-

OTHER PUBLICATIONS

Bumcrot, D. A. and A. McMahon, "Sonic hedgehog: Making the gradient", *Chem. Biol.* 3(1):13–16 (Jan. 1996).

Bumcrot, D. A. and A. McMahon, "Somite differentiation. Sonic signals somites", *Curr. Biol.* 5(6):612–614 (Jun. 1995).

Charité, J. et al., "Ectopic expression of Hoxb–8 causes duplication of the ZPA in the forelimb and homeotic transformation of axial structures", *Cell* 78:589–601 (1994).

Coffman, et al., "Xotch, the Xenopus homolog of Drosophila notch", *Science* 249:1438–1441 (1990).

Concordet, J. and P. Ingham, "Developmental biology. Patterning goes sonic", *Nature* 375(6529):279–280 (May 1995).

Curry, et al., "Sequence analysis reveals homology between two proteins of the flagellar radial spoke", *Mol. Cell. Biol.* 12:3967–3977 (1992).

Davidson, E. H., "How embryos work: a comparative view of diverse modes of cell fate specification", *Develop.* 108:365–389 (1990).

Davis, A. P. and M. R. Capecchi," Axial homeosis and appendicular skeleton defects in mice with a targeted disruption of hoxd–1", *Devel.* 120:2187–2198 (1994).

Dickinson, W., "Molecules and morphology: Where's the homology", *TIG* 11(4):119–120 (1995).

Dingemanse, M. A. et al., "The expression of liver–specific genes within rat embryonic hepatocytes is a discontinous process", *Differentiation* 56:153–162 (1994).

Dollé, P. et al., "Coordinate expression of the murine Hox–5 complex homeobox–containing genes during limb pattern formation", *Nature* 342:767–772 (1989).

Dollé, P. et al., "Disruption of the Hoxd–13 gene induces localized heterochrony leading to mice with neotenic limbs", *Cell* 75:431–441 (1993).

Echelard, Y. et al., "Sonic hedgehog, a member of a family of putative signaling molecules, is implicated in the regulation of CNS polarity", *Cell* 75:1417–1430 (1993).

Ekker, S. et al., "Distinct expression and shared activities of members of the hedgehog gene family of xenopus laevis", *Devel.* 121(8):2337–2347 (Aug. 1995).

Ericson, J. et al., "Sonic hedgehog induces the differentiation of ventral forebrain neurons: a common signal for ventral patterning within the neural tube", *Cell* 81(5):747–756 (Jun. 1995).

Ettelaie, C. et al., "The effect of lipid peroxidation and lipolysis on the ability of lipoproteins to influence thromboplastin activity", *Biochim. Biophys. Acta.* 1257(1):25–30 (Jun. 1995).

Fahmer, K. et al., "Transcription of H–2 and Qa genes in embryonic and adult mice", *EMBO J.* 6:1265–1271 (1987).

Fallon, J. F. et al., "FGF–2: Apical ectodermal ridge growth signal for chick limb development", *Science* 264:104–107 (1994).

Fan, C. et al., "Long–range sclerotome induction by sonic hedgehog: Direct role of the amino–terminal cleavage product and modulation by the cyclic AMP signaling pathway", *Cell* 81:457–65 (May 5, 1995).

Fietz, M. et al., "The hedgehog gene family in Drosophila and vertebrate development", *Devel. (Suppl.)*:43–51 (1994).

Forbes, A. J. et al., "Genetic analysis of hedgehog signaling in the Drosophila embryo", *Devel.* 119(Suppl.):115–124 (1993).

Francis, P. H. et al., "Bone morphogenetic proteins and a signaling pathway that controls patterning in the developing chick limb", *Devel.* 120:209–218 (1994).

Gallop, M. et al., "Applications of combinatorial technologies to drug discovery. 1. Background and peptide combinatorial libraries", *J. Med. Chem.* 37(9):1233–1251 (1994).

Gérard, M. et al., "Structure and activity of regulatory elements involved in the activation of the Hoxd–11 gene during late gastrulation", *EMBO J.* 12:3539–3550 (1993).

Gurdon, J. B., "The generation of diversity and pattern in animal development", *Cell* 68:185–199 (1992).

Halpern, M. E. "Induction of muscle pioneers and floor plate is distinguished by the zebrafish no tail mutation", *Cell* 75:99–111 (1993).

Gustin, K. et al., "Charaterization of the role of individual protein binding motifs within the hepatitis B virus enhancer 1 on X promoter activity using linker scanning mutagenesis", *Virology* 193:653–660 (1993).

Hall, T. et al., "A potential catalytic site revealed by the 1.7–A crystal structure of the amino–terminal signaling domain of sonic hedgehog", *Nature* 378(6553):212–216 (Nov. 1995).

Hamburger, V. and H. L. Hamilton, "A series of normal stages in the development of the chick embryo", *J. Morph.* 88:49–92 (1951).

Hammerschmidt, M. et al., "The world according to hedgehog", *TIG* 13(1):14–21 (1997).

Haramis, A. et al., "The limb deformity mutation disrupts the SHH/ FGF–4 feedback loop and regulation of 5' HoxD genes during limb pattern formation", *Devel.* 121(12):4161–4170 (Dec. 1995).

Hardy, A. et al., "Gene expression, polarising activity and skeletal patterning in reaggregated hind limb mesenchyme", *Devel.* 121(12):4329–4337 (Dec. 1995).

Harmon, C. S. et al., "Evidence that activation of protein kinase A inhibits human hair follicle growth and hair fibre production in organ culture and DNA synthesis in human and mouse hair follicle organ culture", *British J. Dermatol.* 136:853–858 (1997).

Hatta, K. et al., "The cyclops mutation blocks specification of the floor plate of the zebrafish central nervous system", *Nature* 350:339–341 (1991).

Heberlein, U. et al., "The TGBβ homology dpp and the segment polarity gene hedgehog are required for propagation of a morphogenetic wave in the Drosophila retina", *Cell* 75:913–926 (1993).

Heemskerk, J. and S. DiNardo, "Drosophila hedgehog acts as a morphogen in cellular patterning", *Cell* 76:449–460 (1994).

Hidalgo, A. and P. Ingham, "Cell patterning in the Drosophila segment: spatial regulation of the segment polarity gene patched", *Devel.* 110:291–301 (1990).

Hooper, J. and M. Scott, "The Drosophila patched gene encodes a putative membrane protein required for segmental patterning", *Cell* 59:751–765 (1989).

Hynes, R. O., "Integrins: A family of cell surface receptors", *Cell* 48:549–554 (1987).

Hynes, R. O., "Induction of midbrain dopaminergic neurons by Sonic hedgehog", *Neuron* 15(1):35–44 (Jul. 1995).

Ingham, P. W., "Signaling by hedgehog family proteins in Drosophila and vertebrate development", *Curr. Opin. Genet. Dev.* 5(4):478–484 (Aug. 1995).

Ingham, P. W., "Hedgehog points the way", *Current Biology* 4(4):347–350 (1994).

Ingham, P. W., "Localized Hedgehog activity controls spatial limits of wingless transcription in the Drosophila embryo", *Nature 366*:560–562 (1993).

Ingham, P. W. and A. Hidalgo, "Regulation of wingless transcription in the Drosophila embryo", *Devel. 117*:283–291 (1993).

Ingham, P. W. et al., "Role of the Drosophila patched gene in positional signaling", *Nature 353*:184–187 (1991).

Izpisúa– Belmonte, J.–C. et al., "Expression of the homeobox Hox–4 genes and the specification of position in chick wing development", *Nature 350*:585–589 (1991).

Izpisúa– Belmonte, J.–C. et al., "Expression of Hox–4 genes in the chick wings links pattern formation to the epithelial–mesenchymal interaction that mediate growth", *EMBO J. 11*:1451–1457 (1992).

Jiang, J. and G. Struhl, "Protein kinase A in hedgehog signaling in Drosophila limb development", *Cell 80*(4):563–572 (Feb. 1995).

Jessel, T. M. and D. A. Melton, "Diffusible factors in vertebrate embryonic induction", *Cell 68*:257–270 (1992).

Johnson, R. L. and C. Tabin, "The long and short of hedgehog signaling", *Cell 81*:313–315 (May 5, 1995).

Johnson, R. L. et al., "Patched overexpression alters wing disc size and pattern: transcriptional and post–transcriptional effects on hedgehog targets", *Devel. 121*(12):4237–4245 (Dec. 1995).

Johnson, R. L. et al., "Ectopic expression of sonic hedgehog alters dorsal–ventral patterning of somites", *Cell 79*(7):1165–1173 (Dec. 1994).

Johnson, R. L. et al., "Mechanism of limb patterning", *Curr. Opin. Genet. Dev. 4*(4):535–542 (Aug. 1994).

Johnson, R. L. et al., "Sonic hedgehog: a key mediator of anterior–posterior patterning of the limb and dorso–ventral patterning of axial embryonic structures" *Biochem. Soc. Trans. 22*(3):569–574 (Aug. 1994).

Jones, M. et al., "Involvement of bone morphogenetic protein–4 (BMP–4) and Vgr–1 in morphogenesis and neurogenesis in the mouse", Devel. *111*:531–542 (1991).

Kalderon, D.,"Morphogenetic signalling. Responses to hedgehog" *Curr. Biol. 5*(6):580–582 (Jun. 1995).

Koonin, E., "A protein splice–junction motif in hedgehog family proteins", *Trends Biochem. Sci. 20*(4):141–142 (Apr. 1995).

Kornblihtt, A. R. et al., "Primary structure of human fibronectin: differential splicing may generate at least 10 polypeptides from a single gene", *EMBO J. 4*:1755–1759 (1985).

Kornfeld, R. and S. Kornfeld, "Assembly of asparagine–linked oligosaccharides", *Ann. Rev. Biochem. 54*:631–664 (1985).

Krauss, S. et al., "Expression of the zebrafish paired box gene pax[zf–b] during early neurogenesis", *Devel. 113*:1193–1206 (1991).

Krauss, S. et al., "A functionally conserved homolog of the Drosophila Segment polarity gene hh is expressed in tissues with polarizing activity in zebrafish embryos", *Cell 75*:1431–1444 (1993).

Lai, C. et al., "Patterning of the neural ectoderm of *Xenopus laevis* by the amino–terminal product of hedgehog autoproteolytic cleavage", *Devel. 121*:2349–2360 (1995).

Laufer, E. et al., "Sonic hedgehog and Fgf–4 act through a signaling cascade and feedback loop to integrate growth and patterning of the developing limb bud", *Cell 79*:993–1003 (Dec. 16, 1994).

Lee, J. J. et al., "Secretion and localized transcription suggest a role in positional signaling for products of the segmentation gene hedgehog", *Cell 71*:33–50 (1992).

Lee, J. J. et al., "Autoproteolysis in hedgehog protein biogenesis", *Science 266*(5190):1528–1537 (Dec. 1994).

Lee, S. J. "Expression of growth/ differentiation factor 1 in the nervous system: Conservation of a bicistronic structure", *Proc. Natl. Acad. Sci. USA 88*:4250–4254 (Year).

Levin, M. et al., "A molecular pathway determining left–right asymmetry in chick embryogenesis", *Cell 82*(5):803–814 (Sep. 8, 1995).

Li, W. et al., "Function of protein kinase A in hedgehog signal transduction and drosophila imaginal disc development", *Cell 80*(4):553–562(Feb. 1995).

Lopez–Martinez, A. et al., "Limb–patterning activity and restricted posterior localization of the amino–terminal product of sonic hedgehog cleavage", *Curr. Biol. 5*(7):791–796 (Jul. 1995).

Lumsden, A. and A. Graham, "Neural patterning: A forward role for hedgehog", *Curr. Biol. 5*(12):1347–1350 (Dec. 1995).

Ma, C. et al.,"Molecular cloning and characterization of rKlk10, a cDNA encoding T–kininogenase from rat submandibular gland and kidney", *Biochem. 31*(44):10922–10928 (1992).

Ma, C. et al., "The segment polarity gene hedgehog is required for the progression of the morphogenetic furrow in the developing Drosophila eye", *Cell 75*:927–938 (1993).

Ma, C. and K. Moses, "Wingless and patched are negative regulators of the morphogenetic furrow and can affect tissue polarity in the developing Drosophila compound eye", *Devel. 121*(8):2279–2289 (Aug. 1995).

Marigo, V. et al., "Biochemical evidence that patched is the hedgehog receptor", *Nature 384*:176–179 (1996).

Maccabe, J. A. and B. W. Parker, "The target tissue of limb–bud polarizing activity in the induction of supernumerary structures", *J. Embryol. Exp. Morph. 53*:67–73 (1979).

Maiese, K. et al., "Protein kinases modulate the sensitivity of hippocampal neurons to nitric oxide toxicity and anoxia", *J. Neurosci. Res. 36*:77–87 (1993).

Marti, E. et al., "Distribution of Sonic hedgehog peptides in the developing chick and mouse embryo", *Devel. 121*(8):2537–2547 (Aug. 1995).

Marti, E. et al., "Requirement of 19K form of Sonic hedgehog for induction of distinct ventral cell types in CNS explants", *Nature 375*(6529):322–325 (May 1995).

Mavillio, F. et al. "Activation of four homeobox gene clusters in human embryonal carcinoma cells induced to differentiate by retinoic acid", *Differentiation 37*:73–79 (1988).

McGinnis, W. and R. Krumlauf, "Homeobox genes and axial patterning", *Cell 68*:283–302 (1992).

Mohler, J., "Requirements for hedgehog, a segmental polarity gene, in patterning larval and adult cuticle of drosophila", *Genetics 120*:1061–1072 (1988).

Mohler, J. and K. Vani, "Molecular organization and embryonic expression of the hedgehog gene involved in cell–cell communication in segmental patterning of Drosophila", *Devel. 115*:957–971 (1992).

Morgan, B. A. et al., "Targeted misexpression of Hox–4.6 in the avian limb bud causes apparent homeotic transformation", *Nature 358*:236–239 (1992).

Nakano, Y. et al., "A protein with several possible membrane–spanning domains encoded by the Drosophila segment polarity gene patched", *Nature 341*:508–513 (1989).

Ngo, J. et al., "Computational Complexity Protein", Merz and LeGrand, ed. @ Birkhause Boston (1994).

Niswander, L. and G. R. Martin, "FGF–4 and BMP–2 have opposite effects on limb growth", *Nature 361*:68–71(1993).

Niswander, L. et al., "A positive feedback loop coordinates growth and patterning in the vertebrate limb", *Nature, 371*:609–612 (Oct. 13, 1994).

Nohno, T. et al., "Involvement of the Chox–4 Chicken Homeobox Genes in Determination of Anteroposterior Axial Polarity during Limb Development", *Cell*, vol. 64: 1197–1205 (Mar. 22, 1991).

Nohno, T. et al., "Involvement of the Sonic hedgehog gene in chick feather formation", *Biochem. Biophys. Res. Comm. 206*(1): 33–39 (Jan. 1995).

O'Farrell, P. H., "Unanimity waits in the wings", *Nature 368*:188–189 (1994).

Parisi, M. H. et al., "The role of the hedgehog/patched signaling pathway in epithelial stem cell proliferation: From fly to human", *Cell Res. 8*:15–21 (1998).

Parr, B. A. et al., "Mouse Wnt genes exhibit discrete domains of expression in the early embryonic CNS and limb buds", *Development 119*:247–261 (1993).

Patel, N. H. et al., "The role of segment polarity genes during Drosophila neurogenesis", *Genes & Devel. 3*:890–904 (1989).

Peifer, M., "The two faces of hedgehog", *Science 266*(5190):1492–1493 (Dec. 1994).

Perrimon, N. et al.,"Generating lineage–specific markers to study Drosophila development", *Develop. Genet., 12*:238–252 (1991).

Perrimon, N., "Hedgehog and beyond", *Cell 80*:517–520 (Feb. 24, 1995).

Pham, A. et al., "The Suppressor of fused gene encodes a novel PEST protein involved in Drosophila segment polarity estabishment" *Genetics 140*(2):587–598 (Jun. 1995).

Phillis, J. W. and M. H. O'Regan, "Mechanisms of glutamate and aspartate release in the ischemic rat cerebral cortex", *Brain Res. 730*:150–164 (1996).

Placzek, M. et al.,"Induction of floor plate differentiation by contact–dependent, homeogenetic signals", *Development 117*: 205 218 (1993).

Placzek, M. et al., "Orientation of Commissural Axons in vitro in response to a floor plate–derived chemoattractant", *Develop. 110*:19–30 (1990).

Pollock, R. A. et al., "Altering the boundaries of Hox3.1 expression: Evidence for antipodal gene regulation", *Cell 71*: 911–923 (1992).

Porter, J. et al. "The product of hedgehog autoproteolytic cleavage active in local and long–range signalling", *Nature 374*(6520):363–366 (Mar. 23, 1995).

Reeck, et al., "'Homology' in proteins and nucleic acids: A terminology muddle and a way out of it", *Cell 50*:667 (Aug. 28, 1987).

Rennie, J., "Super Sonic", *Sci. Amer*.p. 20, (Apr. 1994).

Riddle, R. D. et al.,"Sonic hedgehog mediates the polarizing activity of the ZPA", *Cell 75*:1401–1416, (Dec. 31, 1993).

Riddle, R. D. et al. "Induction of the LIM homeobox gene Lmx1 by WNT7a establishes dorsoventral pattern in the vertebrate limb", *Cell 83*:631–640 (Nov. 17, 1995).

Riley, B. B. et al., "Retroviral expression of FGF–2 (bFGF) affects patterning in chick limb bud", *Develop. 118*:95–104 (1993).

Roberts, D. et al., "Sonic hedgehog is an endodermal signal inducing Bmp–4 and Hox genes during induction and regionalization of the chick hindgut", *Develop. 121*(10):3163–3174 (Oct. 1995).

Roelink, H. et al, "Floor plate and motor neuron induction vhh–1, a vertebrate homolog of hedgehog expressed by the notochord", *Cell 76*:761–775 (Feb. 25, 1994).

Roelink, H. et al., "Floor plate and motor neuron induction by different concentrations of the amino–terminal cleavage product of sonic hedgehog autoproteolysis", *Cell0 81*:445–455(May 5, 1995).

Sachiko, I. et al., "Sonic hedehog is expressed in epithelial cells during development of whisker, hair and tooth", *Biochem. Biophys. Res. Commun. 218*:688–693 (1996).

Satoh, S. et al., "Neuroprotective properties of a protein kinase inhibitor against ischaemia–induced nueronal damage in rats and gerbils", *Br. J. Pharmacol. 118*:1592–1596 (1996).

St. Jacques, B. et al.,"Sonic hedgehog signaling is essential for hair development", *Curr. Biol. 8*:1058–1068 (1998).

Sasaki, H. and B. L. M. Hogan, "Differential expression of multiple fork head related genes during gastrulation and axial pattern formation in the mouse embryo", *Develop. 118*:47–59 (1993).

Savage, M. et al., "Distribution of FGF–2 suggests is has a role in chick limb bud growth", *Devel. Dynamics 198*:159–170 (1993).

Schuske, K. et al., "Patched overexpression causes loss of wingless expression in drosophila embryos", *Devel. Biol.* 164 : 300–311 (1994).

Smith, J. C., "Hedgehog, the floor plate, and the zone of polarizing activity", *Cell 76*:193–196 (1994).

Stachel, s. E. et al., "Lithium perturbation and goosecoid expression identify a dorsal specification pathway in the pregastrula zebrafish", *Develop. 117*:1261–1274 (1993).

Stolow, M. and Shi. Y., "Xenopus sonic hedgehog as a potential morphogen during embryogenesis and thyroid hormone–dependent metamorphosis", *Nucl. Acids Res. 23*(13):2555–2562 (1995).

Tabata, T. and T.B. Kornberg, "Hedgehog is a signaling protein with a key role in patterning drosophila imaginal discs", *Cell 76*:89–102 (1994).

Tabata, T. et al., "The Drosophila hedgehog gene is expressed specifically in posterior compartment cells and is a target of engrailed regulation", *Genes & Develop. 6*:2635–2645 (1992).

Tabin, C. J., "Retinoids homeoboxes, and growth factors: Toward molecular models for limb development", *Cell 66*:199–217 (Jul. 26, 1991).

Tanabe, Y. et al.,"Induction of motor neurons by sonic hedgehog is independent of floor plate differentiation", *Curr. Biol. 5*(6):651–658 (Jun. 1995).

Tanaka, E. and A. Gann, "Limb development : The budding role of FGF", *Curr. Biol. 5*(6):594–597 (Jun. 1995).

Tashiro, S. et al.,"Structure and expression of hedgehog, a Drosophila segment–polarity gene required for cell–cell communication", *Gene 124*:183–189 (1993).

Taylor, A. M. et al., "Contrasting distributions of patched and hedgehog proteins in the Drosophila embryo", *Mech. Develop. 42*: 89–96 (1993).

Thaller, C. and G. Eichele, "Identification and spatial distrbution of retinoids in the developing chick limb bud", *Nature 327* : 625–628(1987).

Thummel, et al., "Vectors for Drosophila P–element–mediated transformation and tissue culture transfection", *Gene 74*:445–456 (1988).

Tickle, C. et al., "A quantitative analysis of the effect of all–trans–retinoic acid on the pattern of chick wing development", *Develop. Biol. 109*:82–95 (1985).

Tickle, C. et al., "Vertebrate limb development", *Curr. Opin. Genet. Dev.* 5(4):478–484 (1995).

Tickle, C. and G. Eichle, "Vertebrate limb development", *Ann. Rev. Cell Biol. 10*:121–152(1994).

Van Straaten, H. W. M. et al., "Effect of the notochord on the differentiation of a floor plate area in the neural tube of the chick embryo", *Anal. Embryol. 177*:317–324 (1988).

Vogel, A. and C. Tickle, "FGF–4 Maintains polarizing activity of posterior limb bud cells in vivo and in vitro", *Develop.119*:199–206 (1993).

Wallace, et al., "Oligonucleotide probes for the screening of recombinant DNA libraries", *Methods in Enzymol. 152*:432–443 (1987).

Wanek, N. et al., "Conversion by retinoic acid of anterior cells into ZPA cells in the chick wing bud", *Nature 350*:81–83 (Mar. 7, 1991).

Wang, M. et al., "Induction of dopaminergic neuron phenotype in the midbrain by sonic hedgehog protein", *Nature Med. 1*(11):1184–1188 (Nov. 1995).

Yamada, T. et al., "Control of cell pattern in the developing nervous system: Polarizing activity of the floor plate and notochord", *Cell, 64*:635–647, (Feb. 8, 1991).

Yang, Y. and L. Niswander, "Interaction between the signaling molecules WNTZ7a and SHH during vertebtate limb development: dorsal signals regulate anteroposterior patterning", *Cell 80*:939–947 (Mar. 24, 1995).

Yun–Bo Shi, "Cell–cell and cell ECM interactions in epithelial apoptosis and cell renewal during frog intestinal development", *Cell Biochem. Biophys*.27:179–202 (1995).

Zappavigna, et al.,"Hox4 genes encode transcription factors with potential auto– and cross–regulatory capacities", *EMBO J*. 10(13):4177–4187 (1991).

Zardoya, et al.,"Evolution and orthology of hedgehog genes", *TIG* 12(12):496–497 (1996).

Zecca, M. et al., "Sequential organizing activities of engrailed, hedgehog and decapentaplegic in the Drosophila wing", Dev. 121:2265–2278 (Aug. 1995).

\* cited by examiner

SEQUENCE LISTING

<160> NUMBER OF SEQ ID NOS: 26

<210> SEQ ID NO 1
<211> LENGTH: 1277
<212> TYPE: DNA
<213> ORGANISM: chicken Shh
<220> FEATURE:
<221> NAME/KEY: CDS
<222> LOCATION: (1)..(1275)

<400> SEQUENCE: 1

```
atg gtc gaa atg ctg ctg ttg aca aga att ctc ttg gtg ggc ttc atc        48
Met Val Glu Met Leu Leu Leu Thr Arg Ile Leu Leu Val Gly Phe Ile
  1               5                  10                  15 tgc gct ctt tta gtc tcc tct ggg ctg act tgt gga cca ggc agg ggc        96
Cys Ala Leu Leu Val Ser Ser Gly Leu Thr Cys Gly Pro Gly Arg Gly
             20                  25                  30 att gga aaa agg agg cac ccc aaa aag ctg acc ccg tta gcc tat aag       144
Ile Gly Lys Arg Arg His Pro Lys Lys Leu Thr Pro Leu Ala Tyr Lys
         35                  40                  45 cag ttt att ccc aat gtg gca gag aag acc cta ggg gcc agt gga aga       192
Gln Phe Ile Pro Asn Val Ala Glu Lys Thr Leu Gly Ala Ser Gly Arg
     50                  55                  60 tat gaa ggg aag atc aca aga aac tcc gag aga ttt aaa gaa cta acc       240
Tyr Glu Gly Lys Ile Thr Arg Asn Ser Glu Arg Phe Lys Glu Leu Thr
 65                  70                  75                  80 cca aat tac aac cct gac att att ttt aag gat gaa gag aac acg gga       288
Pro Asn Tyr Asn Pro Asp Ile Ile Phe Lys Asp Glu Glu Asn Thr Gly
                 85                  90                  95 gct gac aga ctg atg act cag cgc tgc aag gac aag ctg aat gcc ctg       336
Ala Asp Arg Leu Met Thr Gln Arg Cys Lys Asp Lys Leu Asn Ala Leu
            100                 105                 110 gcg atc tcg gtg atg aac cag tgg ccc ggg gtg aag ctg cgg gtg acc       384
Ala Ile Ser Val Met Asn Gln Trp Pro Gly Val Lys Leu Arg Val Thr
        115                 120                 125 gag ggc tgg gac gag gat ggc cat cac tcc gag gaa tcg ctg cac tac       432
Glu Gly Trp Asp Glu Asp Gly His His Ser Glu Glu Ser Leu His Tyr
    130                 135                 140 gag ggt cgc gcc gtg gac atc acc acg tcg gat cgg gac cgc agc aag       480
Glu Gly Arg Ala Val Asp Ile Thr Thr Ser Asp Arg Asp Arg Ser Lys
145                 150                 155                 160 tac gga atg ctg gcc cgc ctc gcc gtc gag gcc ggc ttc gac tgg gtc       528
Tyr Gly Met Leu Ala Arg Leu Ala Val Glu Ala Gly Phe Asp Trp Val
```

```
                     165                 170                 175
tac tac gag tcc aag gcg cac atc cac tgc tcc gtc aaa gca gaa aac      576
Tyr Tyr Glu Ser Lys Ala His Ile His Cys Ser Val Lys Ala Glu Asn
            180                 185                 190 tca gtg gca gcg aaa tca gga ggc tgc ttc cct ggc tca gcc aca gtg      624
Ser Val Ala Ala Lys Ser Gly Gly Cys Phe Pro Gly Ser Ala Thr Val
            195                 200                 205 cac ctg gag cat gga ggc acc aag ctg gtg aag gac ctg agc cct ggg      672
His Leu Glu His Gly Gly Thr Lys Leu Val Lys Asp Leu Ser Pro Gly
        210                 215                 220 gac cgc gtg ctg gct gct gac gcg gac ggc cgg ctg ctc tac agt gac      720
Asp Arg Val Leu Ala Ala Asp Ala Asp Gly Arg Leu Leu Tyr Ser Asp
225                 230                 235                 240 ttc ctc acc ttc ctc gac cgg atg gac agc tcc cga aag ctc ttc tac      768
Phe Leu Thr Phe Leu Asp Arg Met Asp Ser Ser Arg Lys Leu Phe Tyr
                245                 250                 255 gtc atc gag acg cgg cag ccc cgg gcc cgg ctg cta ctg acg gcg gcc      816
Val Ile Glu Thr Arg Gln Pro Arg Ala Arg Leu Leu Leu Thr Ala Ala
            260                 265                 270 cac ctg ctc ttt gtg gcc ccc cag cac aac cag tcg gag gcc aca ggg      864
His Leu Leu Phe Val Ala Pro Gln His Asn Gln Ser Glu Ala Thr Gly
        275                 280                 285 tcc acc agt ggc cag gcg ctc ttc gcc agc aac gtg aag cct ggc caa      912
Ser Thr Ser Gly Gln Ala Leu Phe Ala Ser Asn Val Lys Pro Gly Gln
    290                 295                 300 cgt gtc tat gtg ctg ggc gag ggc ggg cag cag ctg ctg ccg gcg tct      960
Arg Val Tyr Val Leu Gly Glu Gly Gly Gln Gln Leu Leu Pro Ala Ser
305                 310                 315                 320 gtc cac agc gtc tca ttg cgg gag gag gcg tcc gga gcc tac gcc cca     1008
Val His Ser Val Ser Leu Arg Glu Glu Ala Ser Gly Ala Tyr Ala Pro
                325                 330                 335 ctc acc gcc cag ggc acc atc ctc atc aac cgg gtg ttg gcc tcc tgc     1056
Leu Thr Ala Gln Gly Thr Ile Leu Ile Asn Arg Val Leu Ala Ser Cys
            340                 345                 350 tac gcc gtc atc gag gag cac agt tgg gcc cat tgg gcc ttc gca cca     1104
Tyr Ala Val Ile Glu Glu His Ser Trp Ala His Trp Ala Phe Ala Pro
        355                 360                 365 ttc cgc ttg gct cag ggg ctg ctg gcc gcc ctc tgc cca gat ggg gcc     1152
Phe Arg Leu Ala Gln Gly Leu Leu Ala Ala Leu Cys Pro Asp Gly Ala
    370                 375                 380 atc cct act gcc gcc acc acc acc act ggc atc cat tgg tac tca cgg     1200
Ile Pro Thr Ala Ala Thr Thr Thr Thr Gly Ile His Trp Tyr Ser Arg
385                 390                 395                 400 ctc ctc tac cgc atc ggc agc tgg gtg ctg gat ggt gac gcg ctg cat     1248
Leu Leu Tyr Arg Ile Gly Ser Trp Val Leu Asp Gly Asp Ala Leu His
                405                 410                 415 ccg ctg ggc atg gtg gca ccg gcc agc tg                              1277
Pro Leu Gly Met Val Ala Pro Ala Ser
            420                 425

<210> SEQ ID NO 2
<211> LENGTH: 1191
<212> TYPE: DNA
<213> ORGANISM: murine Dhh
<220> FEATURE:
<221> NAME/KEY: CDS
<222> LOCATION: (1)..(1188)

<400> SEQUENCE: 2 atg gct ctg ccg gcc agt ctg ttg ccc ctg tgc tgc ttg gca ctc ttg       48
Met Ala Leu Pro Ala Ser Leu Leu Pro Leu Cys Cys Leu Ala Leu Leu
```

-continued

|   | 1 | 5 | 10 | 15 |   |
|---|---|---|---|---|---|
| gca cta tct gcc cag agc tgc ggg ccg ggc cga gga ccg gtt ggc cgg<br>Ala Leu Ser Ala Gln Ser Cys Gly Pro Gly Arg Gly Pro Val Gly Arg<br>20 25 30 | | | | | 96 |
| cgg cgt tat gtg cgc aag caa ctt gtg cct ctg cta tac aag cag ttt<br>Arg Arg Tyr Val Arg Lys Gln Leu Val Pro Leu Leu Tyr Lys Gln Phe<br>35 40 45 | | | | | 144 |
| gtg ccc agt atg ccc gag cgg acc ctg ggc gcg agt ggg cca gcg gag<br>Val Pro Ser Met Pro Glu Arg Thr Leu Gly Ala Ser Gly Pro Ala Glu<br>50 55 60 | | | | | 192 |
| ggg agg gta aca agg ggg tcg gag cgc ttc cgg gac ctc gta ccc aac<br>Gly Arg Val Thr Arg Gly Ser Glu Arg Phe Arg Asp Leu Val Pro Asn<br>65 70 75 80 | | | | | 240 |
| tac aac ccc gac ata atc ttc aag gat gag gag aac agc ggc gca gac<br>Tyr Asn Pro Asp Ile Ile Phe Lys Asp Glu Glu Asn Ser Gly Ala Asp<br>85 90 95 | | | | | 288 |
| cgc ctg atg aca gag cgt tgc aaa gag cgg gtg aac gct cta gcc atc<br>Arg Leu Met Thr Glu Arg Cys Lys Glu Arg Val Asn Ala Leu Ala Ile<br>100 105 110 | | | | | 336 |
| gcg gtg atg aac atg tgg ccc gga gta cgc cta cgt gtg act gaa ggc<br>Ala Val Met Asn Met Trp Pro Gly Val Arg Leu Arg Val Thr Glu Gly<br>115 120 125 | | | | | 384 |
| tgg gac gag gac ggc cac cac gca cag gat tca ctc cac tac gaa ggc<br>Trp Asp Glu Asp Gly His His Ala Gln Asp Ser Leu His Tyr Glu Gly<br>130 135 140 | | | | | 432 |
| cgt gcc ttg gac atc acc acg tct gac cgt gac cgt aat aag tat ggt<br>Arg Ala Leu Asp Ile Thr Thr Ser Asp Arg Asp Arg Asn Lys Tyr Gly<br>145 150 155 160 | | | | | 480 |
| ttg ttg gcg cgc cta gct gtg gaa gcc gga ttc gac tgg gtc tac tac<br>Leu Leu Ala Arg Leu Ala Val Glu Ala Gly Phe Asp Trp Val Tyr Tyr<br>165 170 175 | | | | | 528 |
| gag tcc cgc aac cac atc cac gta tcg gtc aaa gct gat aac tca ctg<br>Glu Ser Arg Asn His Ile His Val Ser Val Lys Ala Asp Asn Ser Leu<br>180 185 190 | | | | | 576 |
| gcg gtc cga gcc gga ggc tgc ttt ccg gga aat gcc acg gtg cgc ttg<br>Ala Val Arg Ala Gly Gly Cys Phe Pro Gly Asn Ala Thr Val Arg Leu<br>195 200 205 | | | | | 624 |
| cgg agc ggc gaa cgg aag ggg ctg agg gaa cta cat cgt ggt gac tgg<br>Arg Ser Gly Glu Arg Lys Gly Leu Arg Glu Leu His Arg Gly Asp Trp<br>210 215 220 | | | | | 672 |
| gta ctg gcc gct gat gca gcg ggc cga gtg gta ccc acg cca gtg ctg<br>Val Leu Ala Ala Asp Ala Ala Gly Arg Val Val Pro Thr Pro Val Leu<br>225 230 235 240 | | | | | 720 |
| ctc ttc ctg gac cgg gat ctg cag cgc cgc gcc tcg ttc gtg gct gtg<br>Leu Phe Leu Asp Arg Asp Leu Gln Arg Arg Ala Ser Phe Val Ala Val<br>245 250 255 | | | | | 768 |
| gag acc gag cgg cct ccg cgc aaa ctg ttg ctc aca ccc tgg cat ctg<br>Glu Thr Glu Arg Pro Pro Arg Lys Leu Leu Leu Thr Pro Trp His Leu<br>260 265 270 | | | | | 816 |
| gtg ttc gct gct cgc ggg cca gcg cct gct cca ggt gac ttt gca ccg<br>Val Phe Ala Ala Arg Gly Pro Ala Pro Ala Pro Gly Asp Phe Ala Pro<br>275 280 285 | | | | | 864 |
| gtg ttc gcg cgc cgc tta cgt gct ggc gac tcg gtg ctg gct ccc ggc<br>Val Phe Ala Arg Arg Leu Arg Ala Gly Asp Ser Val Leu Ala Pro Gly<br>290 295 300 | | | | | 912 |
| ggg gac gcg ctc cag ccg gcg cgc gta gcc cgc gtg gcg cgc gag gaa<br>Gly Asp Ala Leu Gln Pro Ala Arg Val Ala Arg Val Ala Arg Glu Glu<br>305 310 315 320 | | | | | 960 |
| gcc gtg ggc gtg ttc gca ccg ctc act gcg cac ggg acg ctg ctg gtc | | | | | 1008 |

-continued

```
                Ala Val Gly Val Phe Ala Pro Leu Thr Ala His Gly Thr Leu Leu Val
                            325                 330                 335 aac gac gtc ctc gcc tcc tgc tac gcg gtt cta gag agt cac cag tgg       1056
Asn Asp Val Leu Ala Ser Cys Tyr Ala Val Leu Glu Ser His Gln Trp
            340                 345                 350 gcc cac cgc gcc ttc gcc cct ttg cgg ctg ctg cac gcg ctc ggg gct       1104
Ala His Arg Ala Phe Ala Pro Leu Arg Leu Leu His Ala Leu Gly Ala
        355                 360                 365 ctg ctc cct ggg ggt gca gtc cag ccg act ggc atg cat tgg tac tct       1152
Leu Leu Pro Gly Gly Ala Val Gln Pro Thr Gly Met His Trp Tyr Ser
    370                 375                 380 cgc ctc ctt tac cgc ttg gcc gag gag tta atg ggc tga                   1191
Arg Leu Leu Tyr Arg Leu Ala Glu Glu Leu Met Gly
385                 390                 395

<210> SEQ ID NO 3
<211> LENGTH: 1281
<212> TYPE: DNA
<213> ORGANISM: murine Ihh
<220> FEATURE:
<221> NAME/KEY: CDS
<222> LOCATION: (1)..(1233)

<400> SEQUENCE: 3 atg tct ccc gcc tgg ctc cgg ccc cga ctg cgg ttc tgt ctg ttc ctg       48
Met Ser Pro Ala Trp Leu Arg Pro Arg Leu Arg Phe Cys Leu Phe Leu
  1               5                  10                  15 ctg ctg ctg ctt ctg gtg ccg gcg gcg cgg ggc tgc ggg ccg ggc cgg       96
Leu Leu Leu Leu Leu Val Pro Ala Ala Arg Gly Cys Gly Pro Gly Arg
                20                  25                  30 gtg gtg ggc agc cgc cgg agg ccg cct cgc aag ctc gtg cct ctt gcc       144
Val Val Gly Ser Arg Arg Arg Pro Pro Arg Lys Leu Val Pro Leu Ala
            35                  40                  45 tac aag cag ttc agc ccc aac gtg ccg gag aag acc ctg ggc gcc agc       192
Tyr Lys Gln Phe Ser Pro Asn Val Pro Glu Lys Thr Leu Gly Ala Ser
        50                  55                  60 ggg cgc tac gaa ggc aag atc gcg cgc agc tct gag cgc ttc aaa gag       240
Gly Arg Tyr Glu Gly Lys Ile Ala Arg Ser Ser Glu Arg Phe Lys Glu
    65                  70                  75                  80 ctc acc ccc aac tac aat ccc gac atc atc ttc aag gac gag gag aac       288
Leu Thr Pro Asn Tyr Asn Pro Asp Ile Ile Phe Lys Asp Glu Glu Asn
                    85                  90                  95 acg ggt gcc gac cgc ctc atg acc cag cgc tgc aag gac cgt ctg aac       336
Thr Gly Ala Asp Arg Leu Met Thr Gln Arg Cys Lys Asp Arg Leu Asn
                100                 105                 110 tca ctg gcc atc tct gtc atg aac cag tgg cct ggt gtg aaa ctg cgg       384
Ser Leu Ala Ile Ser Val Met Asn Gln Trp Pro Gly Val Lys Leu Arg
            115                 120                 125 gtg acc gaa ggc cgg gat gaa gat ggc cat cac tca gag gag tct tta       432
Val Thr Glu Gly Arg Asp Glu Asp Gly His His Ser Glu Glu Ser Leu
        130                 135                 140 cac tat gag ggc cgc gcg gtg gat atc acc acc tca gac cgt gac cga       480
His Tyr Glu Gly Arg Ala Val Asp Ile Thr Thr Ser Asp Arg Asp Arg
145                 150                 155                 160 aat aag tat gga ctg ctg gcg cgc tta gca gtg gag gcc ggc ttc gac       528
Asn Lys Tyr Gly Leu Leu Ala Arg Leu Ala Val Glu Ala Gly Phe Asp
                    165                 170                 175 tgg gtg tat tac gag tcc aag gcc cac gtg cat tgc tct gtc aag tct       576
Trp Val Tyr Tyr Glu Ser Lys Ala His Val His Cys Ser Val Lys Ser
                180                 185                 190 gag cat tcg gcc gct gcc aag aca ggt ggc tgc ttt cct gcc gga gcc       624
Glu His Ser Ala Ala Ala Lys Thr Gly Gly Cys Phe Pro Ala Gly Ala
```

-continued

| | |
|---|---|
| Glu His Ser Ala Ala Ala Lys Thr Gly Gly Cys Phe Pro Ala Gly Ala<br>        195                    200                    205 | |
| cag gtg cgc cta gag aac ggg gag cgt gtg gcc ctg tca gct gta aag<br>Gln Val Arg Leu Glu Asn Gly Glu Arg Val Ala Leu Ser Ala Val Lys<br>210                    215                    220 | 672 |
| cca gga gac cgg gtg ctg gcc atg ggg gag gat ggg acc ccc acc ttc<br>Pro Gly Asp Arg Val Leu Ala Met Gly Glu Asp Gly Thr Pro Thr Phe<br>225              230                    235                    240 | 720 |
| agt gat gtg ctt att ttc ctg gac cgc gag cca aac cgg ctg aga gct<br>Ser Asp Val Leu Ile Phe Leu Asp Arg Glu Pro Asn Arg Leu Arg Ala<br>                  245                    250                    255 | 768 |
| ttc cag gtc atc gag act cag gat cct ccg cgt cgg ctg gcg ctc acg<br>Phe Gln Val Ile Glu Thr Gln Asp Pro Pro Arg Arg Leu Ala Leu Thr<br>        260                    265                    270 | 816 |
| cct gcc cac ctg ctc ttc att gcg gac aat cat aca gaa cca gca gcc<br>Pro Ala His Leu Leu Phe Ile Ala Asp Asn His Thr Glu Pro Ala Ala<br>275                    280                    285 | 864 |
| cac ttc cgg gcc aca ttt gcc agc cat gtg caa cca ggc caa tat gtg<br>His Phe Arg Ala Thr Phe Ala Ser His Val Gln Pro Gly Gln Tyr Val<br>            290                    295                    300 | 912 |
| ctg gta tca ggg gta cca ggc ctc cag cct gct cgg gtg gca gct gtc<br>Leu Val Ser Gly Val Pro Gly Leu Gln Pro Ala Arg Val Ala Ala Val<br>305                    310                    315                    320 | 960 |
| tcc acc cac gtg gcc ctt ggg tcc tat gct cct ctc aca agg cat ggg<br>Ser Thr His Val Ala Leu Gly Ser Tyr Ala Pro Leu Thr Arg His Gly<br>                  325                    330                    335 | 1008 |
| aca ctt gtg gtg gag gat gtg gtg gcc tcc tgc ttt gca gct gtg gct<br>Thr Leu Val Val Glu Asp Val Val Ala Ser Cys Phe Ala Ala Val Ala<br>            340                    345                    350 | 1056 |
| gac cac cat ctg gct cag ttg gcc ttc tgg ccc ctg cga ctg ttt ccc<br>Asp His His Leu Ala Gln Leu Ala Phe Trp Pro Leu Arg Leu Phe Pro<br>355                    360                    365 | 1104 |
| agt ttg gca tgg ggc agc tgg acc cca agt gag ggt gtt cac tcc tac<br>Ser Leu Ala Trp Gly Ser Trp Thr Pro Ser Glu Gly Val His Ser Tyr<br>        370                    375                    380 | 1152 |
| cct cag atg ctc tac cgc ctg ggg cgt ctc ttg cta gaa gag agc acc<br>Pro Gln Met Leu Tyr Arg Leu Gly Arg Leu Leu Leu Glu Glu Ser Thr<br>385                    390                    395                    400 | 1200 |
| ttc cat cca ctg ggc atg tct ggg gca gga agc tgaagggact ctaaccactg<br>Phe His Pro Leu Gly Met Ser Gly Ala Gly Ser<br>                  405                    410 | 1253 |
| ccctcctgga actgctgtgc gtggatcc | 1281 |

<210> SEQ ID NO 4
<211> LENGTH: 1313
<212> TYPE: DNA
<213> ORGANISM: murine Shh
<220> FEATURE:
<221> NAME/KEY: CDS
<222> LOCATION: (1)..(1311)

<400> SEQUENCE: 4

| | |
|---|---|
| atg ctg ctg ctg ctg gcc aga tgt ttt ctg gtg atc ctt gct tcc tcg<br>Met Leu Leu Leu Leu Ala Arg Cys Phe Leu Val Ile Leu Ala Ser Ser<br>1                  5                    10                    15 | 48 |
| ctg ctg gtg tgc ccc ggg ctg gcc tgt ggg ccc ggc agg ggg ttt gga<br>Leu Leu Val Cys Pro Gly Leu Ala Cys Gly Pro Gly Arg Gly Phe Gly<br>                  20                    25                    30 | 96 |
| aag agg cgg cac ccc aaa aag ctg acc cct tta gcc tac aag cag ttt<br>Lys Arg Arg His Pro Lys Lys Leu Thr Pro Leu Ala Tyr Lys Gln Phe<br>        35                    40                    45 | 144 |

-continued

| | | |
|---|---|---|
| att ccc aac gta gcc gag aag acc cta ggg gcc agc ggc aga tat gaa<br>Ile Pro Asn Val Ala Glu Lys Thr Leu Gly Ala Ser Gly Arg Tyr Glu<br>50              55                  60 | 192 | |
| ggg aag atc aca aga aac tcc gaa cga ttt aag gaa ctc acc ccc aat<br>Gly Lys Ile Thr Arg Asn Ser Glu Arg Phe Lys Glu Leu Thr Pro Asn<br>65              70                  75              80 | 240 | |
| tac aac ccc gac atc ata ttt aag gat gag gaa aac acg gga gca gac<br>Tyr Asn Pro Asp Ile Ile Phe Lys Asp Glu Glu Asn Thr Gly Ala Asp<br>            85                  90              95 | 288 | |
| cgg ctg atg act cag agg tgc aaa gac aag tta aat gcc ttg gcc atc<br>Arg Leu Met Thr Gln Arg Cys Lys Asp Lys Leu Asn Ala Leu Ala Ile<br>        100                 105             110 | 336 | |
| tct gtg atg aac cag tgg cct gga gtg agg ctg cga gtg acc gag ggc<br>Ser Val Met Asn Gln Trp Pro Gly Val Arg Leu Arg Val Thr Glu Gly<br>    115                 120             125 | 384 | |
| tgg gat gag gac ggc cat cat tca gag gag tct cta cac tat gag ggt<br>Trp Asp Glu Asp Gly His His Ser Glu Glu Ser Leu His Tyr Glu Gly<br>130             135                 140 | 432 | |
| cga gca gtg gac atc acc acg tcc gac cgg gac cgc agc aag tac ggc<br>Arg Ala Val Asp Ile Thr Thr Ser Asp Arg Asp Arg Ser Lys Tyr Gly<br>145             150                 155             160 | 480 | |
| atg ctg gct cgc ctg gct gtg gaa gca ggt ttc gac tgg gtc tac tat<br>Met Leu Ala Arg Leu Ala Val Glu Ala Gly Phe Asp Trp Val Tyr Tyr<br>            165                 170             175 | 528 | |
| gaa tcc aaa gct cac atc cac tgt tct gtg aaa gca gag aac tcc gtg<br>Glu Ser Lys Ala His Ile His Cys Ser Val Lys Ala Glu Asn Ser Val<br>        180                 185             190 | 576 | |
| gcg gcc aaa tcc ggc ggc tgt ttc ccg gga tcc gcc acc gtg cac ctg<br>Ala Ala Lys Ser Gly Gly Cys Phe Pro Gly Ser Ala Thr Val His Leu<br>    195                 200             205 | 624 | |
| gag cag ggc ggc acc aag ctg gtg aag gac tta cgt ccc gga gac cgc<br>Glu Gln Gly Gly Thr Lys Leu Val Lys Asp Leu Arg Pro Gly Asp Arg<br>210             215                 220 | 672 | |
| gtg ctg gcg gct gac gac cag ggc cgg ctg ctg tac agc gac ttc ctc<br>Val Leu Ala Ala Asp Asp Gln Gly Arg Leu Leu Tyr Ser Asp Phe Leu<br>225             230                 235             240 | 720 | |
| acc ttc ctg gac cgc gac gaa ggc gcc aag aag gtc ttc tac gtg atc<br>Thr Phe Leu Asp Arg Asp Glu Gly Ala Lys Lys Val Phe Tyr Val Ile<br>            245                 250             255 | 768 | |
| gag acg ctg gag ccg cgc gag cgc ctg ctg ctc acc gcc gcg cac ctg<br>Glu Thr Leu Glu Pro Arg Glu Arg Leu Leu Leu Thr Ala Ala His Leu<br>        260                 265             270 | 816 | |
| ctc ttc gtg gcg ccg cac aac gac tcg ggg ccc acg ccc ggg cca agc<br>Leu Phe Val Ala Pro His Asn Asp Ser Gly Pro Thr Pro Gly Pro Ser<br>    275                 280             285 | 864 | |
| gcg ctc ttt gcc agc cgc gtg cgc ccc ggg cag cgc gtg tac gtg gtg<br>Ala Leu Phe Ala Ser Arg Val Arg Pro Gly Gln Arg Val Tyr Val Val<br>290             295                 300 | 912 | |
| gct gaa cgc ggc ggg gac cgc cgg ctg ctg ccc gcc gcg gtg cac agc<br>Ala Glu Arg Gly Gly Asp Arg Arg Leu Leu Pro Ala Ala Val His Ser<br>305             310                 315             320 | 960 | |
| gtg acg ctg cga gag gag gag gcg ggc gcg tac gcg ccg ctc acg gcg<br>Val Thr Leu Arg Glu Glu Glu Ala Gly Ala Tyr Ala Pro Leu Thr Ala<br>            325                 330             335 | 1008 | |
| cac ggc acc att ctc atc aac cgg gtg ctc gcc tcg tgc tac gct gtc<br>His Gly Thr Ile Leu Ile Asn Arg Val Leu Ala Ser Cys Tyr Ala Val<br>        340                 345             350 | 1056 | |
| atc gag gag cac agc tgg gca cac cgg gcc ttc gcg cct ttc cgc ctg<br>Ile Glu Glu His Ser Trp Ala His Arg Ala Phe Ala Pro Phe Arg Leu | 1104 | |

-continued

```
                    355                  360                  365
gcg cac gcg ctg ctg gcc gcg ctg gca ccc gcc cgc acg gac ggc ggg      1152
Ala His Ala Leu Leu Ala Ala Leu Ala Pro Ala Arg Thr Asp Gly Gly
        370                  375                  380 ggc ggg ggc agc atc cct gca gcg caa tct gca acg gaa gcg agg ggc      1200
Gly Gly Gly Ser Ile Pro Ala Ala Gln Ser Ala Thr Glu Ala Arg Gly
385                  390                  395                  400 gcg gag ccg act gcg ggc atc cac tgg tac tcg cag ctg ctc tac cac      1248
Ala Glu Pro Thr Ala Gly Ile His Trp Tyr Ser Gln Leu Leu Tyr His
                405                  410                  415 att ggc acc tgg ctg ttg gac agc gag acc atg cat ccc ttg gga atg      1296
Ile Gly Thr Trp Leu Leu Asp Ser Glu Thr Met His Pro Leu Gly Met
            420                  425                  430 gcg gtc aag tcc agc tg                                               1313
Ala Val Lys Ser Ser
        435

<210> SEQ ID NO 5
<211> LENGTH: 1256
<212> TYPE: DNA
<213> ORGANISM: zebrafish Shh
<220> FEATURE:
<221> NAME/KEY: CDS
<222> LOCATION: (1)..(1254)

<400> SEQUENCE: 5 atg cgg ctt ttg acg aga gtg ctg ctg gtg tct ctt ctc act ctg tcc       48
Met Arg Leu Leu Thr Arg Val Leu Leu Val Ser Leu Leu Thr Leu Ser
  1               5                  10                  15 ttg gtg gtg tcc gga ctg gcc tgc ggt cct ggc aga ggc tac ggc aga       96
Leu Val Val Ser Gly Leu Ala Cys Gly Pro Gly Arg Gly Tyr Gly Arg
                 20                  25                  30 aga aga cat ccg aag aag ctg aca cct ctc gcc tac aag cag ttc ata      144
Arg Arg His Pro Lys Lys Leu Thr Pro Leu Ala Tyr Lys Gln Phe Ile
             35                  40                  45 cct aat gtc gcg gag aag acc tta ggg gcc agc ggc aga tac gag ggc      192
Pro Asn Val Ala Glu Lys Thr Leu Gly Ala Ser Gly Arg Tyr Glu Gly
         50                  55                  60 aag ata acg cgc aat tcg gag aga ttt aaa gaa ctt act cca aat tac      240
Lys Ile Thr Arg Asn Ser Glu Arg Phe Lys Glu Leu Thr Pro Asn Tyr
 65                  70                  75                  80 aat ccc gac att atc ttt aag gat gag gag aac acg gga gcg gac agg      288
Asn Pro Asp Ile Ile Phe Lys Asp Glu Glu Asn Thr Gly Ala Asp Arg
                 85                  90                  95 ctc atg aca cag aga tgc aaa gac aag ctg aac tcg ctg gcc atc tct      336
Leu Met Thr Gln Arg Cys Lys Asp Lys Leu Asn Ser Leu Ala Ile Ser
            100                 105                 110 gta atg aac cac tgg cca ggg gtt aag ctg cgt gtg aca gag ggc tgg      384
Val Met Asn His Trp Pro Gly Val Lys Leu Arg Val Thr Glu Gly Trp
        115                 120                 125 gat gag gac ggt cac cat ttt gaa gaa tca ctc cac tac gag gga aga      432
Asp Glu Asp Gly His His Phe Glu Glu Ser Leu His Tyr Glu Gly Arg
    130                 135                 140 gct gtt gat att acc acc tct gac cga gac aag agc aaa tac ggg aca      480
Ala Val Asp Ile Thr Thr Ser Asp Arg Asp Lys Ser Lys Tyr Gly Thr
145                 150                 155                 160 ctg tct cgc cta gct gtg gag gct gga ttt gac tgg gtc tat tac gag      528
Leu Ser Arg Leu Ala Val Glu Ala Gly Phe Asp Trp Val Tyr Tyr Glu
                165                 170                 175 tcc aaa gcc cac att cat tgc tct gtc aaa gca gaa aat tcg gtt gct      576
Ser Lys Ala His Ile His Cys Ser Val Lys Ala Glu Asn Ser Val Ala
```

-continued

```
                        180                     185                     190
gcg aaa tct ggg ggc tgt ttc cca ggt tcg gct ctg gtc tcg ctc cag         624
Ala Lys Ser Gly Gly Cys Phe Pro Gly Ser Ala Leu Val Ser Leu Gln
            195                     200                     205 gac gga gga cag aag gcc gtg aag gac ctg aac ccc gga gac aag gtg         672
Asp Gly Gly Gln Lys Ala Val Lys Asp Leu Asn Pro Gly Asp Lys Val
    210                     215                     220 ctg gcg gca gac agc gcg gga aac ctg gtg ttc agc gac ttc atc atg         720
Leu Ala Ala Asp Ser Ala Gly Asn Leu Val Phe Ser Asp Phe Ile Met
225                     230                     235                     240 ttc aca gac cga gac tcc acg acg cga cgt gtg ttt tac gtc ata gaa         768
Phe Thr Asp Arg Asp Ser Thr Thr Arg Arg Val Phe Tyr Val Ile Glu
                    245                     250                     255 acg caa gaa ccc gtt gaa aag atc acc ctc acc gcc gct cac ctc ctt         816
Thr Gln Glu Pro Val Glu Lys Ile Thr Leu Thr Ala Ala His Leu Leu
                260                     265                     270 ttt gtc ctc gac aac tca acg gaa gat ctc cac acc atg acc gcc gcg         864
Phe Val Leu Asp Asn Ser Thr Glu Asp Leu His Thr Met Thr Ala Ala
            275                     280                     285 tat gcc agc agt gtc aga gcc gga caa aag gtg atg gtt gtt gat gat         912
Tyr Ala Ser Ser Val Arg Ala Gly Gln Lys Val Met Val Val Asp Asp
        290                     295                     300 agc ggt cag ctt aaa tct gtc atc gtg cag cgg ata tac acg gag gag         960
Ser Gly Gln Leu Lys Ser Val Ile Val Gln Arg Ile Tyr Thr Glu Glu
305                     310                     315                     320 cag cgg ggc tcg ttc gca cca gtg act gca cat ggg acc att gtg gtc        1008
Gln Arg Gly Ser Phe Ala Pro Val Thr Ala His Gly Thr Ile Val Val
                    325                     330                     335 gac aga ata ctg gcg tcc tgt tac gcc gta ata gag gac cag ggg ctt        1056
Asp Arg Ile Leu Ala Ser Cys Tyr Ala Val Ile Glu Asp Gln Gly Leu
                340                     345                     350 gcg cat ttg gcc ttc gcg ccc gcc agg ctc tat tat tac gtg tca tca        1104
Ala His Leu Ala Phe Ala Pro Ala Arg Leu Tyr Tyr Tyr Val Ser Ser
            355                     360                     365 ttc ctg tcc ccc aaa act cca gca gtc ggt cca atg cga ctt tac aac        1152
Phe Leu Ser Pro Lys Thr Pro Ala Val Gly Pro Met Arg Leu Tyr Asn
        370                     375                     380 agg agg ggg tcc act ggt act cca ggc tcc tgt cat caa atg gga acg        1200
Arg Arg Gly Ser Thr Gly Thr Pro Gly Ser Cys His Gln Met Gly Thr
385                     390                     395                     400 tgg ctt ttg gac agc aac atg ctt cat cct ttg ggg atg tca gta aac        1248
Trp Leu Leu Asp Ser Asn Met Leu His Pro Leu Gly Met Ser Val Asn
                    405                     410                     415 tca agc tg                                                             1256
Ser Ser
```

<210> SEQ ID NO 6
<211> LENGTH: 1425
<212> TYPE: DNA
<213> ORGANISM: Homo sapien Shh
<220> FEATURE:
<221> NAME/KEY: CDS
<222> LOCATION: (1)..(1425)
<220> FEATURE:
<223> OTHER INFORMATION: "nnn" encoding "Xaa" at position 1387-1389 may
      be a, t, c, g, other or unknown

<400> SEQUENCE: 6

```
atg ctg ctg ctg gcg aga tgt ctg ctg cta gtc ctc gtc tcc tcg ctg          48
Met Leu Leu Leu Ala Arg Cys Leu Leu Leu Val Leu Val Ser Ser Leu
1               5                   10                  15
```

```
ctg gta tgc tcg gga ctg gcg tgc gga ccg ggc agg ggg ttc ggg aag    96
Leu Val Cys Ser Gly Leu Ala Cys Gly Pro Gly Arg Gly Phe Gly Lys
         20                  25                  30 agg agg cac ccc aaa aag ctg acc cct tta gcc tac aag cag ttt atc   144
Arg Arg His Pro Lys Lys Leu Thr Pro Leu Ala Tyr Lys Gln Phe Ile
     35                  40                  45 ccc aat gtg gcc gag aag acc cta ggc gcc agc gga agg tat gaa ggg   192
Pro Asn Val Ala Glu Lys Thr Leu Gly Ala Ser Gly Arg Tyr Glu Gly
 50                  55                  60 aag atc tcc aga aac tcc gag cga ttt aag gaa ctc acc ccc aat tac   240
Lys Ile Ser Arg Asn Ser Glu Arg Phe Lys Glu Leu Thr Pro Asn Tyr
 65                  70                  75                  80 aac ccc gac atc ata ttt aag gat gaa gaa aac acc gga gcg gac agg   288
Asn Pro Asp Ile Ile Phe Lys Asp Glu Glu Asn Thr Gly Ala Asp Arg
                 85                  90                  95 ctg atg act cag agg tgt aag gac aag ttg aac gct ttg gcc atc tcg   336
Leu Met Thr Gln Arg Cys Lys Asp Lys Leu Asn Ala Leu Ala Ile Ser
            100                 105                 110 gtg atg aac cag tgg cca gga gtg aaa ctg cgg gtg acc gag ggc tgg   384
Val Met Asn Gln Trp Pro Gly Val Lys Leu Arg Val Thr Glu Gly Trp
        115                 120                 125 gac gaa gat ggc cac cac tca gag gag tct ctg cac tac gag ggc cgc   432
Asp Glu Asp Gly His His Ser Glu Glu Ser Leu His Tyr Glu Gly Arg
130                 135                 140 gca gtg gac atc acc acg tct gac cgc gac cgc agc aag tac ggc atg   480
Ala Val Asp Ile Thr Thr Ser Asp Arg Asp Arg Ser Lys Tyr Gly Met
145                 150                 155                 160 ctg gcc cgc ctg gcg gtg gag gcc ggc ttc gac tgg gtg tac tac gag   528
Leu Ala Arg Leu Ala Val Glu Ala Gly Phe Asp Trp Val Tyr Tyr Glu
            165                 170                 175 tcc aag gca cat atc cac tgc tcg gtg aaa gca gag aac tcg gtg gcg   576
Ser Lys Ala His Ile His Cys Ser Val Lys Ala Glu Asn Ser Val Ala
        180                 185                 190 gcc aaa tcg gga ggc tgc ttc ccg ggc tcg gcc acg gtg cac ctg gag   624
Ala Lys Ser Gly Gly Cys Phe Pro Gly Ser Ala Thr Val His Leu Glu
    195                 200                 205 cag ggc ggc acc aag ctg gtg aag gac ctg agc ccc ggg gac cgc gtg   672
Gln Gly Gly Thr Lys Leu Val Lys Asp Leu Ser Pro Gly Asp Arg Val
210                 215                 220 ctg gcg gcg gac gac cag ggc cgg ctg ctc tac agc gac ttc ctc act   720
Leu Ala Ala Asp Asp Gln Gly Arg Leu Leu Tyr Ser Asp Phe Leu Thr
225                 230                 235                 240 ttc ctg gac cgc gac gac ggc gcc aag aag gtc ttc tac gtg atc gag   768
Phe Leu Asp Arg Asp Asp Gly Ala Lys Lys Val Phe Tyr Val Ile Glu
            245                 250                 255 acg cgg gag ccg cgc gag cgc ctg ctc acc gcc gcg cac ctg ctc       816
Thr Arg Glu Pro Arg Glu Arg Leu Leu Leu Thr Ala Ala His Leu Leu
        260                 265                 270 ttt gtg gcg ccg cac aac gac tcg gcc acc ggg gag ccc gag gcg tcc   864
Phe Val Ala Pro His Asn Asp Ser Ala Thr Gly Glu Pro Glu Ala Ser
    275                 280                 285 tcg ggc tcg ggg ccg cct tcc ggg ggc gca ctg ggg cct cgg gcg ctg   912
Ser Gly Ser Gly Pro Pro Ser Gly Gly Ala Leu Gly Pro Arg Ala Leu
290                 295                 300 ttc gcc agc cgc gtg cgc ccg ggc cag cgc gtg tac gtg gtg gcc gag   960
Phe Ala Ser Arg Val Arg Pro Gly Gln Arg Val Tyr Val Val Ala Glu
305                 310                 315                 320 cgt gac ggg gac cgc cgg ctc ctg ccc gcc gct gtg cac agc gtg acc  1008
Arg Asp Gly Asp Arg Arg Leu Leu Pro Ala Ala Val His Ser Val Thr
            325                 330                 335
```

-continued

```
cta agc gag gag gcc gcg ggc gcc tac gcg ccg ctc acg gcc cag ggc        1056
Leu Ser Glu Glu Ala Ala Gly Ala Tyr Ala Pro Leu Thr Ala Gln Gly
        340                 345                 350 acc att ctc atc aac cgg gtg ctg gcc tcg tgc tac gcg gtc atc gag        1104
Thr Ile Leu Ile Asn Arg Val Leu Ala Ser Cys Tyr Ala Val Ile Glu
    355                 360                 365 gag cac agc tgg gcg cac cgg gcc ttc gcg ccc ttc cgc ctg gcg cac        1152
Glu His Ser Trp Ala His Arg Ala Phe Ala Pro Phe Arg Leu Ala His
370                 375                 380 gcg ctc ctg gct gca ctg gcg ccc gcg cgc acg gac cgc ggg ggg gac        1200
Ala Leu Leu Ala Ala Leu Ala Pro Ala Arg Thr Asp Arg Gly Gly Asp
385                 390                 395                 400 agc ggc ggc ggg gac cgc ggg ggc ggc ggc aga gta gcc cta acc            1248
Ser Gly Gly Gly Asp Arg Gly Gly Gly Gly Arg Val Ala Leu Thr
            405                 410                 415 gct cca ggt gct gcc gac gct ccg ggt gcg ggg gcc acc gcg ggc atc        1296
Ala Pro Gly Ala Ala Asp Ala Pro Gly Ala Gly Ala Thr Ala Gly Ile
            420                 425                 430 cac tgg tac tcg cag ctg ctc tac caa ata ggc acc tgg ctc ctg gac        1344
His Trp Tyr Ser Gln Leu Leu Tyr Gln Ile Gly Thr Trp Leu Leu Asp
        435                 440                 445 agc gag gcc ctg cac ccg ctg ggc atg gcg gtc aag tcc agc nnn agc        1392
Ser Glu Ala Leu His Pro Leu Gly Met Ala Val Lys Ser Ser Xaa Ser
    450                 455                 460 cgg ggg gcc ggg gga ggg gcg cgg gag ggg gcc                            1425
Arg Gly Ala Gly Gly Gly Ala Arg Glu Gly Ala
465                 470                 475

<210> SEQ ID NO 7
<211> LENGTH: 1622
<212> TYPE: DNA
<213> ORGANISM: Homo sapien Ihh
<220> FEATURE:
<221> NAME/KEY: CDS
<222> LOCATION: (51)..(1283)

<400> SEQUENCE: 7
catcagccca ccaggagacc tcgcccgccg ctcccccggg ctccccggcc atg tct         56
                                                        Met Ser
                                                        1 ccc gcc cgg ctc cgg ccc cga ctg cac ttc tgc ctg gtc ctg ttg ctg       104
Pro Ala Arg Leu Arg Pro Arg Leu His Phe Cys Leu Val Leu Leu Leu
        5                   10                  15 ctg ctg gtg gtg ccc gcg gca tgg ggc tgc ggg ccg ggt cgg gtg gtg       152
Leu Leu Val Val Pro Ala Ala Trp Gly Cys Gly Pro Gly Arg Val Val
    20                  25                  30 ggc agc cgc cgg cga ccg cca cgc aaa ctc gtg ccg ctc gcc tac aag       200
Gly Ser Arg Arg Arg Pro Pro Arg Lys Leu Val Pro Leu Ala Tyr Lys
35                  40                  45                  50 cag ttc agc ccc aat gtg ccc gag aag acc ctg ggc gcc agc gga cgc       248
Gln Phe Ser Pro Asn Val Pro Glu Lys Thr Leu Gly Ala Ser Gly Arg
                55                  60                  65 tat gaa ggc aag atc gct cgc agc tcc gag cgc ttc aag gag ctc acc       296
Tyr Glu Gly Lys Ile Ala Arg Ser Ser Glu Arg Phe Lys Glu Leu Thr
            70                  75                  80 ccc aat tac aat cca gac atc atc ttc aag gac gag gag aac aca ggc       344
Pro Asn Tyr Asn Pro Asp Ile Ile Phe Lys Asp Glu Glu Asn Thr Gly
        85                  90                  95 gcc gac cgc ctc atg acc cag cgc tgc aag gac cgc ctg aac tcg ctg       392
Ala Asp Arg Leu Met Thr Gln Arg Cys Lys Asp Arg Leu Asn Ser Leu
    100                 105                 110
```

-continued

| | |
|---|---|
| gct atc tcg gtg atg aac cag tgg ccc ggt gtg aag ctg cgg gtg acc<br>Ala Ile Ser Val Met Asn Gln Trp Pro Gly Val Lys Leu Arg Val Thr<br>115                    120                    125                    130 | 440 |
| gag ggc tgg gac gag gac ggc cac cac tca gag gag tcc ctg cat tat<br>Glu Gly Trp Asp Glu Asp Gly His His Ser Glu Glu Ser Leu His Tyr<br>                    135                    140                    145 | 488 |
| gag ggc cgc gcg gtg gac atc acc aca tca gac cgc gac cgc aat aag<br>Glu Gly Arg Ala Val Asp Ile Thr Thr Ser Asp Arg Asp Arg Asn Lys<br>150                    155                    160 | 536 |
| tat gga ctg ctg gcg cgc ttg gca gtg gag gcc ggc ttt gac tgg gtg<br>Tyr Gly Leu Leu Ala Arg Leu Ala Val Glu Ala Gly Phe Asp Trp Val<br>               165                    170                    175 | 584 |
| tat tac gag tca aag gcc cac gtg cat tgc tcc gtc aag tcc gag cac<br>Tyr Tyr Glu Ser Lys Ala His Val His Cys Ser Val Lys Ser Glu His<br>180                    185                    190 | 632 |
| tcg gcc gca gcc aag acg ggc ggc tgc ttc cct gcc gga gcc cag gta<br>Ser Ala Ala Ala Lys Thr Gly Gly Cys Phe Pro Ala Gly Ala Gln Val<br>195                    200                    205                    210 | 680 |
| cgc ctg gag agt ggg gcg cgt gtg gcc ttg tca gcc gtg agg ccg gga<br>Arg Leu Glu Ser Gly Ala Arg Val Ala Leu Ser Ala Val Arg Pro Gly<br>                    215                    220                    225 | 728 |
| gac cgt gtg ctg gcc atg ggg gag gat ggg agc ccc acc ttc agc gat<br>Asp Arg Val Leu Ala Met Gly Glu Asp Gly Ser Pro Thr Phe Ser Asp<br>230                    235                    240 | 776 |
| gtg ctc att ttc ctg gac cgc gag ccc cac agg ctg aga gcc ttc cag<br>Val Leu Ile Phe Leu Asp Arg Glu Pro His Arg Leu Arg Ala Phe Gln<br>               245                    250                    255 | 824 |
| gtc atc gag act cag gac ccc cca cgc cgc ctg gca ctc aca ccc gct<br>Val Ile Glu Thr Gln Asp Pro Pro Arg Arg Leu Ala Leu Thr Pro Ala<br>260                    265                    270 | 872 |
| cac ctg ctc ttt acg gct gac aat cac acg gag ccg gca gcc cgc ttc<br>His Leu Leu Phe Thr Ala Asp Asn His Thr Glu Pro Ala Ala Arg Phe<br>275                    280                    285                    290 | 920 |
| cgg gcc aca ttt gcc agc cac gtg cag cct ggc cag tac gtg ctg gtg<br>Arg Ala Thr Phe Ala Ser His Val Gln Pro Gly Gln Tyr Val Leu Val<br>                    295                    300                    305 | 968 |
| gct ggg gtg cca ggc ctg cag cct gcc cgc gtg gca gct gtc tct aca<br>Ala Gly Val Pro Gly Leu Gln Pro Ala Arg Val Ala Ala Val Ser Thr<br>310                      315                    320 | 1016 |
| cac gtg gcc ctc ggg gcc tac gcc ccg ctc aca aag cat ggg aca ctg<br>His Val Ala Leu Gly Ala Tyr Ala Pro Leu Thr Lys His Gly Thr Leu<br>               325                    330                    335 | 1064 |
| gtg gtg gag gat gtg gtg gca tcc tgc ttc gcg gcc gtg gct gac cac<br>Val Val Glu Asp Val Val Ala Ser Cys Phe Ala Ala Val Ala Asp His<br>340                    345                    350 | 1112 |
| cac ctg gct cag ttg gcc ttc tgg ccc ctg aga ctc ttt cac agc ttg<br>His Leu Ala Gln Leu Ala Phe Trp Pro Leu Arg Leu Phe His Ser Leu<br>355                    360                    365                    370 | 1160 |
| gca tgg ggc agc tgg acc ccg ggg gag ggt gtg cat tgg tac ccc cag<br>Ala Trp Gly Ser Trp Thr Pro Gly Glu Gly Val His Trp Tyr Pro Gln<br>                    375                    380                    385 | 1208 |
| ctg ctc tac cgc ctg ggg cgt ctc ctg cta gaa gag ggc agc ttc cac<br>Leu Leu Tyr Arg Leu Gly Arg Leu Leu Leu Glu Glu Gly Ser Phe His<br>390                    395                    400 | 1256 |
| cca ctg ggc atg tcc ggg gca ggg agc tgaaaggact ccaccgctgc<br>Pro Leu Gly Met Ser Gly Ala Gly Ser<br>405                    410 | 1303 |
| cctcctggaa ctgctgtact gggtccagaa gcctctcagc caggagggag ctggccctgg | 1363 |

-continued

```
aagggacctg agctggggga cactggctcc tgccatctcc tctgccatga agatacacca      1423
ttgagacttg actgggcaac accagcgtcc cccacccgcg tcgtggtgta gtcatagagc      1483
tgcaagctga gctggcgagg ggatggttgt tgacccctct ctcctagaga ccttgaggct      1543
ggcacggcga ctcccaactc agcctgctct cactacgagt tttcatactc tgcctccccc      1603
attgggaggg cccattccc                                                  1622

<210> SEQ ID NO 8
<211> LENGTH: 1251
<212> TYPE: DNA
<213> ORGANISM: Zebrafish Thh
<220> FEATURE:
<221> NAME/KEY: CDS
<222> LOCATION: (1)..(1248)

<400> SEQUENCE: 8
```

| | | | | | | | | | | | | | | | | |
|---|---|---|---|---|---|---|---|---|---|---|---|---|---|---|---|---|
| atg | gac | gta | agg | ctg | cat | ctg | aag | caa | ttt | gct | tta | ctg | tgt | ttt | atc | 48 |
| Met | Asp | Val | Arg | Leu | His | Leu | Lys | Gln | Phe | Ala | Leu | Leu | Cys | Phe | Ile | |
| 1 | | | | 5 | | | | | 10 | | | | | 15 | | |
| agc | ttg | ctt | ctg | acg | cct | tgt | gga | tta | gcc | tgt | ggt | cct | ggt | aga | ggt | 96 |
| Ser | Leu | Leu | Leu | Thr | Pro | Cys | Gly | Leu | Ala | Cys | Gly | Pro | Gly | Arg | Gly | |
| | | | 20 | | | | | 25 | | | | | 30 | | | |
| tat | gga | aaa | cga | aga | cac | cca | aag | aaa | tta | acc | ccg | ttg | gct | tac | aag | 144 |
| Tyr | Gly | Lys | Arg | Arg | His | Pro | Lys | Lys | Leu | Thr | Pro | Leu | Ala | Tyr | Lys | |
| | 35 | | | | | 40 | | | | | 45 | | | | | |
| caa | ttc | atc | ccc | aac | gtt | gct | gag | aaa | acg | ctt | gga | gcc | agc | ggc | aaa | 192 |
| Gln | Phe | Ile | Pro | Asn | Val | Ala | Glu | Lys | Thr | Leu | Gly | Ala | Ser | Gly | Lys | |
| 50 | | | | | 55 | | | | | 60 | | | | | | |
| tac | gaa | ggc | aaa | atc | aca | agg | aat | tca | gag | aga | ttt | aaa | gag | ctg | att | 240 |
| Tyr | Glu | Gly | Lys | Ile | Thr | Arg | Asn | Ser | Glu | Arg | Phe | Lys | Glu | Leu | Ile | |
| 65 | | | | | 70 | | | | | 75 | | | | | 80 | |
| ccg | aat | tat | aat | ccc | gat | atc | atc | ttt | aag | gac | gag | gaa | aac | aca | aac | 288 |
| Pro | Asn | Tyr | Asn | Pro | Asp | Ile | Ile | Phe | Lys | Asp | Glu | Glu | Asn | Thr | Asn | |
| | | | | 85 | | | | | 90 | | | | | 95 | | |
| gct | gac | agg | ctg | atg | acc | aag | cgc | tgt | aag | gac | aag | tta | aat | tcg | ttg | 336 |
| Ala | Asp | Arg | Leu | Met | Thr | Lys | Arg | Cys | Lys | Asp | Lys | Leu | Asn | Ser | Leu | |
| | | | 100 | | | | | 105 | | | | | 110 | | | |
| gcc | ata | tcc | gtc | atg | aac | cac | tgg | ccc | ggc | gtg | aaa | ctg | cgc | gtc | act | 384 |
| Ala | Ile | Ser | Val | Met | Asn | His | Trp | Pro | Gly | Val | Lys | Leu | Arg | Val | Thr | |
| | | 115 | | | | | 120 | | | | | 125 | | | | |
| gaa | ggc | tgg | gat | gag | gat | ggt | cac | cat | tta | gaa | gaa | tct | ttg | cac | tat | 432 |
| Glu | Gly | Trp | Asp | Glu | Asp | Gly | His | His | Leu | Glu | Glu | Ser | Leu | His | Tyr | |
| | 130 | | | | | 135 | | | | | 140 | | | | | |
| gag | gga | cgg | gca | gtg | gac | atc | act | acc | tca | gac | agg | gat | aaa | agc | aag | 480 |
| Glu | Gly | Arg | Ala | Val | Asp | Ile | Thr | Thr | Ser | Asp | Arg | Asp | Lys | Ser | Lys | |
| 145 | | | | | 150 | | | | | 155 | | | | | 160 | |
| tat | ggg | atg | cta | tcc | agg | ctt | gca | gtg | gag | gca | gga | ttc | gac | tgg | gtc | 528 |
| Tyr | Gly | Met | Leu | Ser | Arg | Leu | Ala | Val | Glu | Ala | Gly | Phe | Asp | Trp | Val | |
| | | | | 165 | | | | | 170 | | | | | 175 | | |
| tat | tat | gaa | tct | aaa | gcc | cac | ata | cac | tgc | tct | gtc | aaa | gca | gaa | aat | 576 |
| Tyr | Tyr | Glu | Ser | Lys | Ala | His | Ile | His | Cys | Ser | Val | Lys | Ala | Glu | Asn | |
| | | | 180 | | | | | 185 | | | | | 190 | | | |
| tca | gtg | gct | gct | aaa | tca | gga | gga | tgt | ttt | cct | ggg | tct | ggg | acg | gtg | 624 |
| Ser | Val | Ala | Ala | Lys | Ser | Gly | Gly | Cys | Phe | Pro | Gly | Ser | Gly | Thr | Val | |
| | | 195 | | | | | 200 | | | | | 205 | | | | |
| aca | ctt | ggt | gat | ggg | acg | agg | aaa | ccc | atc | aaa | gat | ctt | aaa | gtg | ggc | 672 |
| Thr | Leu | Gly | Asp | Gly | Thr | Arg | Lys | Pro | Ile | Lys | Asp | Leu | Lys | Val | Gly | |
| | 210 | | | | | 215 | | | | | 220 | | | | | |
| gac | cgg | gtt | ttg | gct | gca | gac | gag | aag | gga | aat | gtc | tta | ata | agc | gac | 720 |
| Asp | Arg | Val | Leu | Ala | Ala | Asp | Glu | Lys | Gly | Asn | Val | Leu | Ile | Ser | Asp | |

-continued

| | | | | | | | | | | | | | | | | |
|---|---|---|---|---|---|---|---|---|---|---|---|---|---|---|---|---|
| | | 225 | | | | 230 | | | | 235 | | | | 240 | | |
| ttt | att | atg | ttt | ata | gac | cac | gat | ccg | aca | acg | aga | agg | caa | ttc | atc | 768 |
| Phe | Ile | Met | Phe | Ile | Asp | His | Asp | Pro | Thr | Thr | Arg | Arg | Gln | Phe | Ile | |
| | | 245 | | | | 250 | | | | | | 255 | | | | |
| gtc | atc | gag | acg | tca | gaa | cct | ttc | acc | aag | ctc | acc | ctc | act | gcc | gcg | 816 |
| Val | Ile | Glu | Thr | Ser | Glu | Pro | Phe | Thr | Lys | Leu | Thr | Leu | Thr | Ala | Ala | |
| | | | 260 | | | | | 265 | | | | | 270 | | | |
| cac | cta | gtt | ttc | gtt | gga | aac | tct | tca | gca | gct | tcg | ggt | ata | aca | gca | 864 |
| His | Leu | Val | Phe | Val | Gly | Asn | Ser | Ser | Ala | Ala | Ser | Gly | Ile | Thr | Ala | |
| | | 275 | | | | | 280 | | | | | 285 | | | | |
| aca | ttt | gcc | agc | aac | gtg | aag | cct | gga | gat | aca | gtt | tta | gtg | tgg | gaa | 912 |
| Thr | Phe | Ala | Ser | Asn | Val | Lys | Pro | Gly | Asp | Thr | Val | Leu | Val | Trp | Glu | |
| | 290 | | | | | 295 | | | | | 300 | | | | | |
| gac | aca | tgc | gag | agc | ctc | aag | agc | gtt | aca | gtg | aaa | agg | att | tac | act | 960 |
| Asp | Thr | Cys | Glu | Ser | Leu | Lys | Ser | Val | Thr | Val | Lys | Arg | Ile | Tyr | Thr | |
| 305 | | | | | 310 | | | | | 315 | | | | | 320 | |
| gag | gag | cac | gag | ggc | tct | ttt | gcg | cca | gtc | acc | gcg | cac | gga | acc | ata | 1008 |
| Glu | Glu | His | Glu | Gly | Ser | Phe | Ala | Pro | Val | Thr | Ala | His | Gly | Thr | Ile | |
| | | | | 325 | | | | | 330 | | | | | 335 | | |
| ata | gtg | gat | cag | gtg | ttg | gca | tcg | tgc | tac | gcg | gtc | att | gag | aac | cac | 1056 |
| Ile | Val | Asp | Gln | Val | Leu | Ala | Ser | Cys | Tyr | Ala | Val | Ile | Glu | Asn | His | |
| | | | 340 | | | | | 345 | | | | | 350 | | | |
| aaa | tgg | gca | cat | tgg | gct | ttt | gcg | ccg | gtc | agg | ttg | tgt | cac | aag | ctg | 1104 |
| Lys | Trp | Ala | His | Trp | Ala | Phe | Ala | Pro | Val | Arg | Leu | Cys | His | Lys | Leu | |
| | | 355 | | | | | 360 | | | | | 365 | | | | |
| atg | acg | tgg | ctt | ttt | ccg | gct | cgt | gaa | tca | aac | gtc | aat | ttt | cag | gag | 1152 |
| Met | Thr | Trp | Leu | Phe | Pro | Ala | Arg | Glu | Ser | Asn | Val | Asn | Phe | Gln | Glu | |
| | 370 | | | | | 375 | | | | | 380 | | | | | |
| gat | ggt | atc | cac | tgg | tac | tca | aat | atg | ctg | ttt | cac | atc | ggc | tct | tgg | 1200 |
| Asp | Gly | Ile | His | Trp | Tyr | Ser | Asn | Met | Leu | Phe | His | Ile | Gly | Ser | Trp | |
| 385 | | | | | 390 | | | | | 395 | | | | | 400 | |
| ctg | ctg | gac | aga | gac | tct | ttc | cat | cca | ctc | ggg | att | tta | cac | tta | agt | 1248 |
| Leu | Leu | Asp | Arg | Asp | Ser | Phe | His | Pro | Leu | Gly | Ile | Leu | His | Leu | Ser | |
| | | | | 405 | | | | | 410 | | | | | 415 | | |
| tga | | | | | | | | | | | | | | | | 1251 |

<210> SEQ ID NO 9
<211> LENGTH: 1416
<212> TYPE: DNA
<213> ORGANISM: Drosophila HH
<220> FEATURE:
<221> NAME/KEY: CDS
<222> LOCATION: (1)..(1413)

<400> SEQUENCE: 9

| | | | | | | | | | | | | | | | | |
|---|---|---|---|---|---|---|---|---|---|---|---|---|---|---|---|---|
| atg | gat | aac | cac | agc | tca | gtg | cct | tgg | gcc | agt | gcc | gcc | agt | gtc | acc | 48 |
| Met | Asp | Asn | His | Ser | Ser | Val | Pro | Trp | Ala | Ser | Ala | Ala | Ser | Val | Thr | |
| 1 | | | | 5 | | | | | 10 | | | | | 15 | | |
| tgt | ctc | tcc | ctg | gga | tgc | caa | atg | cca | cag | ttc | cag | ttc | cag | ttc | cag | 96 |
| Cys | Leu | Ser | Leu | Gly | Cys | Gln | Met | Pro | Gln | Phe | Gln | Phe | Gln | Phe | Gln | |
| | | | 20 | | | | | 25 | | | | | 30 | | | |
| ctc | caa | atc | cgc | agc | gag | ctc | cat | ctc | cgc | aag | ccc | gca | aga | aga | acg | 144 |
| Leu | Gln | Ile | Arg | Ser | Glu | Leu | His | Leu | Arg | Lys | Pro | Ala | Arg | Arg | Thr | |
| | | 35 | | | | | 40 | | | | | 45 | | | | |
| caa | acg | atg | cgc | cac | att | gcg | cat | acg | cag | cgt | tgc | ctc | agc | agg | ctg | 192 |
| Gln | Thr | Met | Arg | His | Ile | Ala | His | Thr | Gln | Arg | Cys | Leu | Ser | Arg | Leu | |
| | 50 | | | | | 55 | | | | | 60 | | | | | |
| acc | tct | ctg | gtg | gcc | ctg | ctg | ctg | atc | gtc | ttg | ccg | atg | gtc | ttt | agc | 240 |
| Thr | Ser | Leu | Val | Ala | Leu | Leu | Leu | Ile | Val | Leu | Pro | Met | Val | Phe | Ser | |
| 65 | | | | | 70 | | | | | 75 | | | | | 80 | |

-continued

| | | |
|---|---|---|
| ccg gct cac agc tgc ggt cct ggc cga gga ttg ggt cgt cat agg gcg<br>Pro Ala His Ser Cys Gly Pro Gly Arg Gly Leu Gly Arg His Arg Ala<br>85　　　　　　　　　　90　　　　　　　　　　95 | 288 | |
| cgc aac ctg tat ccg ctg gtc ctc aag cag aca att ccc aat cta tcc<br>Arg Asn Leu Tyr Pro Leu Val Leu Lys Gln Thr Ile Pro Asn Leu Ser<br>　　　100　　　　　　　　　　105　　　　　　　　　　110 | 336 | |
| gag tac acg aac agc gcc tcc gga cct ctg gag ggt gtg atc cgt cgg<br>Glu Tyr Thr Asn Ser Ala Ser Gly Pro Leu Glu Gly Val Ile Arg Arg<br>115　　　　　　　　　　120　　　　　　　　　　125 | 384 | |
| gat tcg ccc aaa ttc aag gac ctc gtg ccc aac tac aac agg gac atc<br>Asp Ser Pro Lys Phe Lys Asp Leu Val Pro Asn Tyr Asn Arg Asp Ile<br>　　130　　　　　　　　　　135　　　　　　　　　　140 | 432 | |
| ctt ttc cgt gac gag gaa ggc acc gga gcg gat ggc ttg atg agc aag<br>Leu Phe Arg Asp Glu Glu Gly Thr Gly Ala Asp Gly Leu Met Ser Lys<br>145　　　　　　　　　　150　　　　　　　　　　155　　　　　　　　　　160 | 480 | |
| cgc tgc aag gag aag cta aac gtg ctg gcc tac tcg gtg atg aac gaa<br>Arg Cys Lys Glu Lys Leu Asn Val Leu Ala Tyr Ser Val Met Asn Glu<br>　　　　　　165　　　　　　　　　　170　　　　　　　　　　175 | 528 | |
| tgg ccc ggc atc cgg ctg ctg gtc acc gag agc tgg gac gag gac tac<br>Trp Pro Gly Ile Arg Leu Leu Val Thr Glu Ser Trp Asp Glu Asp Tyr<br>　　　　　180　　　　　　　　　　185　　　　　　　　　　190 | 576 | |
| cat cac ggc cag gag tcg ctc cac tac gag ggc cga gcg gtg acc att<br>His His Gly Gln Glu Ser Leu His Tyr Glu Gly Arg Ala Val Thr Ile<br>　　　　195　　　　　　　　　　200　　　　　　　　　　205 | 624 | |
| gcc acc tcc gat cgc gac cag tcc aaa tac ggc atg ctc gct cgc ctg<br>Ala Thr Ser Asp Arg Asp Gln Ser Lys Tyr Gly Met Leu Ala Arg Leu<br>210　　　　　　　　　　215　　　　　　　　　　220 | 672 | |
| gcc gtc gag gct gga ttc gat tgg gtc tcc tac gtc agc agg cgc cac<br>Ala Val Glu Ala Gly Phe Asp Trp Val Ser Tyr Val Ser Arg Arg His<br>225　　　　　　　　　　230　　　　　　　　　　235　　　　　　　　　　240 | 720 | |
| atc tac tgc tcc gtc aag tca gat tcg tcg atc agt tcc cac gtg cac<br>Ile Tyr Cys Ser Val Lys Ser Asp Ser Ser Ile Ser Ser His Val His<br>　　　　　　245　　　　　　　　　　250　　　　　　　　　　255 | 768 | |
| ggc tgc ttc acg ccg gag agc aca gcg ctg ctg gag agt gga gtc cgg<br>Gly Cys Phe Thr Pro Glu Ser Thr Ala Leu Leu Glu Ser Gly Val Arg<br>　　　　　260　　　　　　　　　　265　　　　　　　　　　270 | 816 | |
| aag ccg ctc ggc gag ctc tct atc gga gat cgt gtt ttg agc atg acc<br>Lys Pro Leu Gly Glu Leu Ser Ile Gly Asp Arg Val Leu Ser Met Thr<br>　　　　275　　　　　　　　　　280　　　　　　　　　　285 | 864 | |
| gcc aac gga cag gcc gtc tac agc gaa gtg atc ctc ttc atg gac cgc<br>Ala Asn Gly Gln Ala Val Tyr Ser Glu Val Ile Leu Phe Met Asp Arg<br>290　　　　　　　　　　295　　　　　　　　　　300 | 912 | |
| aac ctc gag cag atg caa aac ttt gtg cag ctg cac acg gac ggt gga<br>Asn Leu Glu Gln Met Gln Asn Phe Val Gln Leu His Thr Asp Gly Gly<br>305　　　　　　　　　　310　　　　　　　　　　315　　　　　　　　　　320 | 960 | |
| gca gtg ctc acg gtg acg ccg gct cac ctg gtt agc gtt tgg cag ccg<br>Ala Val Leu Thr Val Thr Pro Ala His Leu Val Ser Val Trp Gln Pro<br>　　　　　　325　　　　　　　　　　330　　　　　　　　　　335 | 1008 | |
| gag agc cag aag ctc acg ttt gtg ttt gcg cat cgc atc gag gag aag<br>Glu Ser Gln Lys Leu Thr Phe Val Phe Ala His Arg Ile Glu Glu Lys<br>　　　　　340　　　　　　　　　　345　　　　　　　　　　350 | 1056 | |
| aac cag gtg ctc gta cgg gat gtg gag acg ggc gag ctg agg ccc cag<br>Asn Gln Val Leu Val Arg Asp Val Glu Thr Gly Glu Leu Arg Pro Gln<br>　　　　355　　　　　　　　　　360　　　　　　　　　　365 | 1104 | |
| cga gtg gtc aag ttg ggc agt gtg cgc agt aag ggc gtg gtc gcg ccg<br>Arg Val Val Lys Leu Gly Ser Val Arg Ser Lys Gly Val Val Ala Pro<br>370　　　　　　　　　　375　　　　　　　　　　380 | 1152 | |
| ctg acc cgc gag ggc acc att gtg gtc aac tcg gtg gcc gcc agt tgc<br>Leu Thr Arg Glu Gly Thr Ile Val Val Asn Ser Val Ala Ala Ser Cys<br>385　　　　　　　　　　390　　　　　　　　　　395　　　　　　　　　　400 | 1200 | |

-continued

```
tat gcg gtg atc aac agt cag tcg ctg gcc cac tgg gga ctg gct ccc      1248
Tyr Ala Val Ile Asn Ser Gln Ser Leu Ala His Trp Gly Leu Ala Pro
            405                 410                 415 atg cgc ctg ctg tcc acg ctg gag gcg tgg ctg ccc gcc aag gag cag      1296
Met Arg Leu Leu Ser Thr Leu Glu Ala Trp Leu Pro Ala Lys Glu Gln
        420                 425                 430 ttg cac agt tcg ccg aag gtg gtg agc tcg gcg cag cag cag aat ggc      1344
Leu His Ser Ser Pro Lys Val Val Ser Ser Ala Gln Gln Gln Asn Gly
    435                 440                 445 atc cat tgg tat gcc aat gcg ctc tac aag gtc aag gac tac gtg ctg      1392
Ile His Trp Tyr Ala Asn Ala Leu Tyr Lys Val Lys Asp Tyr Val Leu
450                 455                 460 ccg cag agc tgg cgc cac gat tga                                      1416
Pro Gln Ser Trp Arg His Asp
465                 470
```

<210> SEQ ID NO 10
<211> LENGTH: 425
<212> TYPE: PRT
<213> ORGANISM: chicken Shh

<400> SEQUENCE: 10

```
Met Val Glu Met Leu Leu Leu Thr Arg Ile Leu Leu Val Gly Phe Ile
1               5                   10                  15

Cys Ala Leu Leu Val Ser Ser Gly Leu Thr Cys Gly Pro Gly Arg Gly
            20                  25                  30

Ile Gly Lys Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
    130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
            260                 265                 270
```

```
His Leu Leu Phe Val Ala Pro Gln His Asn Gln Ser Glu Ala Thr Gly
            275                 280                 285

Ser Thr Ser Gly Gln Ala Leu Phe Ala Ser Asn Val Lys Pro Gly Gln
        290                 295                 300

Arg Val Tyr Val Leu Gly Glu Gly Gly Gln Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
            355                 360                 365

Phe Arg Leu Ala Gln Gly Leu Leu Ala Ala Leu Cys Pro Asp Gly Ala
        370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

<210> SEQ ID NO 11
<211> LENGTH: 396
<212> TYPE: PRT
<213> ORGANISM: murine Dhh

<400> SEQUENCE: 11

Met Ala Leu Pro Ala Ser Leu Leu Pro Leu Cys Cys Leu Ala Leu Leu
1               5                   10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
```

```
         210                 215                 220
Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Thr Pro Trp His Leu
            260                 265                 270

Val Phe Ala Ala Arg Gly Pro Ala Pro Ala Pro Gly Asp Phe Ala Pro
                275                 280                 285

Val Phe Ala Arg Arg Leu Arg Ala Gly Asp Ser Val Leu Ala Pro Gly
                290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu His Ala Leu Gly Ala
                355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: murine Ihh

<400> SEQUENCE: 12

Met Ser Pro Ala Trp Leu Arg Pro Arg Leu Arg Phe Cys Leu Phe Leu
1               5                   10                  15

Leu Leu Leu Leu Leu Val Pro Ala Ala Arg Gly Cys Gly Pro Gly Arg
                20                  25                  30

Val Val Gly Ser Arg Arg Pro Arg Lys Leu Val Pro Leu Ala
            35                  40                  45

Tyr Lys Gln Phe Ser Pro Asn Val Pro Glu Lys Thr Leu Gly Ala Ser
            50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
                100                 105                 110

Ser Leu Ala Ile Ser Val Met Asn Gln Trp Pro Gly Val Lys Leu Arg
                115                 120                 125

Val Thr Glu Gly Arg Asp Glu Asp Gly His His Ser Glu Glu Ser Leu
                130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
                180                 185                 190
```

-continued

```
Glu His Ser Ala Ala Ala Lys Thr Gly Gly Cys Phe Pro Ala Gly Ala
            195                 200                 205

Gln Val Arg Leu Glu Asn Gly Glu Arg Val Ala Leu Ser Ala Val Lys
210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
            245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
            275                 280                 285

His Phe Arg Ala Thr Phe Ala Ser His Val Gln Pro Gly Gln Tyr Val
            290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
            325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
            355                 360                 365

Ser Leu Ala Trp Gly Ser Trp Thr Pro Ser Glu Gly Val His Ser Tyr
            370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
            405                 410

<210> SEQ ID NO 13
<211> LENGTH: 437
<212> TYPE: PRT
<213> ORGANISM: murine Shh

<400> SEQUENCE: 13

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
                20                  25                  30

Lys Arg Arg His Pro Lys Lys Leu Thr Pro Leu Ala Tyr Lys Gln Phe
            35                  40                  45

Ile Pro Asn Val Ala Glu Lys Thr Leu Gly Ala Ser Gly Arg Tyr Glu
        50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160
```

```
Met Leu Ala Arg Leu Ala Val Glu Ala Gly Phe Asp Trp Val Tyr Tyr
                165                 170                 175
Glu Ser Lys Ala His Ile His Cys Ser Val Lys Ala Glu Asn Ser Val
            180                 185                 190
Ala Ala Lys Ser Gly Gly Cys Phe Pro Gly Ser Ala Thr Val His Leu
        195                 200                 205
Glu Gln Gly Gly Thr Lys Leu Val Lys Asp Leu Arg Pro Gly Asp Arg
    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Leu Glu Pro Arg Glu Arg Leu Leu Leu Thr Ala Ala His Leu
            260                 265                 270
Leu Phe Val Ala Pro His Asn Asp Ser Gly Pro Thr Pro Gly Pro Ser
        275                 280                 285
Ala Leu Phe Ala Ser Arg Val Arg Pro Gly Gln Arg Val Tyr Val Val
    290                 295                 300
Ala Glu Arg Gly Gly Asp Arg Arg Leu Leu Pro Ala Ala Val His Ser
305                 310                 315                 320
Val Thr Leu Arg Glu Glu Glu Ala Gly Ala Tyr Ala Pro Leu Thr Ala
                325                 330                 335
His Gly Thr Ile Leu Ile Asn Arg Val Leu Ala Ser Cys Tyr Ala Val
            340                 345                 350
Ile Glu Glu His Ser Trp Ala His Arg Ala Phe Ala Pro Phe Arg Leu
        355                 360                 365
Ala His Ala Leu Leu Ala Ala Leu Ala Pro Ala Arg Thr Asp Gly Gly
    370                 375                 380
Gly Gly Gly Ser Ile Pro Ala Ala Gln Ser Ala Thr Glu Ala Arg Gly
385                 390                 395                 400
Ala Glu Pro Thr Ala Gly Ile His Trp Tyr Ser Gln Leu Leu Tyr His
                405                 410                 415
Ile Gly Thr Trp Leu Leu Asp Ser Glu Thr Met His Pro Leu Gly Met
            420                 425                 430
Ala Val Lys Ser Ser
        435

<210> SEQ ID NO 14
<211> LENGTH: 418
<212> TYPE: PRT
<213> ORGANISM: zebrafish Shh

<400> SEQUENCE: 14

Met Arg Leu Leu Thr Arg Val Leu Leu Val Ser Leu Leu Thr Leu Ser
1               5                   10                  15
Leu Val Val Ser Gly Leu Ala Cys Gly Pro Gly Arg Gly Tyr Gly Arg
            20                  25                  30
Arg Arg His Pro Lys Lys Leu Thr Pro Leu Ala Tyr Lys Gln Phe Ile
        35                  40                  45
Pro Asn Val Ala Glu Lys Thr Leu Gly Ala Ser Gly Arg Tyr Glu Gly
    50                  55                  60
Lys Ile Thr Arg Asn Ser Glu Arg Phe Lys Glu Leu Thr Pro Asn Tyr
65                  70                  75                  80
Asn Pro Asp Ile Ile Phe Lys Asp Glu Glu Asn Thr Gly Ala Asp Arg
```

```
                    85                  90                  95
Leu Met Thr Gln Arg Cys Lys Asp Lys Leu Asn Ser Leu Ala Ile Ser
                100                 105                 110
Val Met Asn His Trp Pro Gly Val Lys Leu Arg Val Thr Glu Gly Trp
                115                 120                 125
Asp Glu Asp Gly His His Phe Glu Glu Ser Leu His Tyr Glu Gly Arg
            130                 135                 140
Ala Val Asp Ile Thr Thr Ser Asp Arg Asp Lys Ser Lys Tyr Gly Thr
145                 150                 155                 160
Leu Ser Arg Leu Ala Val Glu Ala Gly Phe Asp Trp Val Tyr Tyr Glu
                165                 170                 175
Ser Lys Ala His Ile His Cys Ser Val Lys Ala Glu Asn Ser Val Ala
                180                 185                 190
Ala Lys Ser Gly Gly Cys Phe Pro Gly Ser Ala Leu Val Ser Leu Gln
            195                 200                 205
Asp Gly Gly Gln Lys Ala Val Lys Asp Leu Asn Pro Gly Asp Lys Val
        210                 215                 220
Leu Ala Ala Asp Ser Ala Gly Asn Leu Val Phe Ser Asp Phe Ile Met
225                 230                 235                 240
Phe Thr Asp Arg Asp Ser Thr Thr Arg Arg Val Phe Tyr Val Ile Glu
                245                 250                 255
Thr Gln Glu Pro Val Glu Lys Ile Thr Leu Thr Ala Ala His Leu Leu
                260                 265                 270
Phe Val Leu Asp Asn Ser Thr Glu Asp Leu His Thr Met Thr Ala Ala
            275                 280                 285
Tyr Ala Ser Ser Val Arg Ala Gly Gln Lys Val Met Val Val Asp Asp
        290                 295                 300
Ser Gly Gln Leu Lys Ser Val Ile Val Gln Arg Ile Tyr Thr Glu Glu
305                 310                 315                 320
Gln Arg Gly Ser Phe Ala Pro Val Thr Ala His Gly Thr Ile Val Val
                325                 330                 335
Asp Arg Ile Leu Ala Ser Cys Tyr Ala Val Ile Glu Asp Gln Gly Leu
            340                 345                 350
Ala His Leu Ala Phe Ala Pro Ala Arg Leu Tyr Tyr Tyr Val Ser Ser
        355                 360                 365
Phe Leu Ser Pro Lys Thr Pro Ala Val Gly Pro Met Arg Leu Tyr Asn
370                 375                 380
Arg Arg Gly Ser Thr Gly Thr Pro Gly Ser Cys His Gln Met Gly Thr
385                 390                 395                 400
Trp Leu Leu Asp Ser Asn Met Leu His Pro Leu Gly Met Ser Val Asn
                405                 410                 415
Ser Ser

<210> SEQ ID NO 15
<211> LENGTH: 475
<212> TYPE: PRT
<213> ORGANISM: Homo sapien Shh
<220> FEATURE:
<223> OTHER INFORMATION: Xaa at position 463 is any or unknown amino
      acid

<400> SEQUENCE: 15

Met Leu Leu Leu Ala Arg Cys Leu Leu Leu Val Leu Val Ser Ser Leu
  1               5                  10                  15

Leu Val Cys Ser Gly Leu Ala Cys Gly Pro Gly Arg Gly Phe Gly Lys
```

```
                    20                  25                  30
Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
 50                  55                  60

Lys Ile Ser Arg Asn Ser Glu Arg Phe Lys Glu Leu Thr Pro Asn Tyr
 65                  70                  75                  80

Asn Pro Asp Ile Ile Phe Lys Asp Glu Asn Thr Gly Ala Asp Arg
                 85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
            115                 120                 125

Asp Glu Asp Gly His His Ser Glu Glu Ser Leu His Tyr Glu Gly Arg
            130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
            165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
            195                 200                 205

Gln Gly Gly Thr Lys Leu Val Lys Asp Leu Ser Pro Gly Asp Arg Val
210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
            245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
            290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
            325                 330                 335

Leu Ser Glu Glu Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
            370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Arg Val Ala Leu Thr
            405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
            435                 440                 445
```

```
Ser Glu Ala Leu His Pro Leu Gly Met Ala Val Lys Ser Ser Xaa Ser
    450                 455                 460

Arg Gly Ala Gly Gly Ala Arg Glu Gly Ala
465                 470                 475

<210> SEQ ID NO 16
<211> LENGTH: 411
<212> TYPE: PRT
<213> ORGANISM: Homo sapien Ihh

<400> SEQUENCE: 16

Met Ser Pro Ala Arg Leu Arg Pro Arg Leu His Phe Cys Leu Val Leu
  1               5                  10                  15

Leu Leu Leu Val Val Pro Ala Ala Trp Gly Cys Gly Pro Gly Arg
             20                  25                  30

Val Val Gly Ser Arg Arg Arg Pro Pro Arg Lys Leu Val Pro Leu Ala
             35                  40                  45

Tyr Lys Gln Phe Ser Pro Asn Val Pro Glu Lys Thr Leu Gly Ala Ser
         50                  55                  60

Gly Arg Tyr Glu Gly Lys Ile Ala Arg Ser Ser Glu Arg Phe Lys Glu
 65                  70                  75                  80

Leu Thr Pro Asn Tyr Asn Pro Asp Ile Ile Phe Lys Asp Glu Asn
                 85                  90                  95

Thr Gly Ala Asp Arg Leu Met Thr Gln Arg Cys Lys Asp Arg Leu Asn
                100                 105                 110

Ser Leu Ala Ile Ser Val Met Asn Gln Trp Pro Gly Val Lys Leu Arg
            115                 120                 125

Val Thr Glu Gly Trp Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
                180                 185                 190

Glu His Ser Ala Ala Ala Lys Thr Gly Gly Cys Phe Pro Ala Gly Ala
            195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
                260                 265                 270

Pro Ala His Leu Leu Phe Thr Ala Asp Asn His Thr Glu Pro Ala Ala
            275                 280                 285

Arg Phe Arg Ala Thr Phe Ala Ser His Val Gln Pro Gly Gln Tyr Val
    290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
```

```
                    340                 345                 350
Asp His His Leu Ala Gln Leu Ala Phe Trp Pro Leu Arg Leu Phe His
            355                 360                 365
Ser Leu Ala Trp Gly Ser Trp Thr Pro Gly Glu Gly Val His Trp Tyr
        370                 375                 380
Pro Gln Leu Leu Tyr Arg Leu Arg Leu Leu Glu Glu Gly Ser
385                 390                 395                 400
Phe His Pro Leu Gly Met Ser Gly Ala Gly Ser
                405                 410

<210> SEQ ID NO 17
<211> LENGTH: 416
<212> TYPE: PRT
<213> ORGANISM: Zebrafish Thh

<400> SEQUENCE: 17

Met Asp Val Arg Leu His Leu Lys Gln Phe Ala Leu Leu Cys Phe Ile
 1               5                  10                  15
Ser Leu Leu Leu Thr Pro Cys Gly Leu Ala Cys Gly Pro Gly Arg Gly
                20                  25                  30
Tyr Gly Lys Arg Arg His Pro Lys Lys Leu Thr Pro Leu Ala Tyr Lys
            35                  40                  45
Gln Phe Ile Pro Asn Val Ala Glu Lys Thr Leu Gly Ala Ser Gly Lys
        50                  55                  60
Tyr Glu Gly Lys Ile Thr Arg Asn Ser Glu Arg Phe Lys Glu Leu Ile
65                  70                  75                  80
Pro Asn Tyr Asn Pro Asp Ile Ile Phe Lys Asp Glu Glu Asn Thr Asn
                85                  90                  95
Ala Asp Arg Leu Met Thr Lys Arg Cys Lys Asp Lys Leu Asn Ser Leu
            100                 105                 110
Ala Ile Ser Val Met Asn His Trp Pro Gly Val Lys Leu Arg Val Thr
        115                 120                 125
Glu Gly Trp Asp Glu Asp Gly His His Leu Glu Glu Ser Leu His Tyr
130                 135                 140
Glu Gly Arg Ala Val Asp Ile Thr Thr Ser Asp Arg Asp Lys Ser Lys
145                 150                 155                 160
Tyr Gly Met Leu Ser Arg Leu Ala Val Glu Ala Gly Phe Asp Trp Val
                165                 170                 175
Tyr Tyr Glu Ser Lys Ala His Ile His Cys Ser Val Lys Ala Glu Asn
            180                 185                 190
Ser Val Ala Ala Lys Ser Gly Gly Cys Phe Pro Gly Ser Gly Thr Val
        195                 200                 205
Thr Leu Gly Asp Gly Thr Arg Lys Pro Ile Lys Asp Leu Lys Val Gly
210                 215                 220
Asp Arg Val Leu Ala Ala Asp Glu Lys Gly Asn Val Leu Ile Ser Asp
225                 230                 235                 240
Phe Ile Met Phe Ile Asp His Asp Pro Thr Thr Arg Arg Gln Phe Ile
                245                 250                 255
Val Ile Glu Thr Ser Glu Pro Phe Thr Lys Leu Thr Leu Thr Ala Ala
            260                 265                 270
His Leu Val Phe Val Gly Asn Ser Ser Ala Ala Ser Gly Ile Thr Ala
        275                 280                 285
Thr Phe Ala Ser Asn Val Lys Pro Gly Asp Thr Val Leu Val Trp Glu
    290                 295                 300
```

-continued

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
            325                 330                 335

Ile Val Asp Gln Val Leu Ala Ser Cys Tyr Ala Val Ile Glu Asn His
            340                 345                 350

Lys Trp Ala His Trp Ala Phe Ala Pro Val Arg Leu Cys His Lys Leu
            355                 360                 365

Met Thr Trp Leu Phe Pro Ala Arg Glu Ser Asn Val Asn Phe Gln Glu
370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
            405                 410                 415

<210> SEQ ID NO 18
<211> LENGTH: 471
<212> TYPE: PRT
<213> ORGANISM: Drosophila HH

<400> SEQUENCE: 18

Met Asp Asn His Ser Ser Val Pro Trp Ala Ser Ala Ala Ser Val Thr
1               5                   10                  15

Cys Leu Ser Leu Gly Cys Gln Met Pro Gln Phe Gln Phe Gln Phe Gln
            20                  25                  30

Leu Gln Ile Arg Ser Glu Leu His Leu Arg Lys Pro Ala Arg Arg Thr
        35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

-continued

```
Lys Pro Leu Gly Glu Leu Ser Ile Gly Asp Arg Val Leu Ser Met Thr
        275                 280                 285
Ala Asn Gly Gln Ala Val Tyr Ser Glu Val Ile Leu Phe Met Asp Arg
        290                 295                 300
Asn Leu Glu Gln Met Gln Asn Phe Val Gln Leu His Thr Asp Gly Gly
305                 310                 315                 320
Ala Val Leu Thr Val Thr Pro Ala His Leu Val Ser Val Trp Gln Pro
                325                 330                 335
Glu Ser Gln Lys Leu Thr Phe Val Phe Ala His Arg Ile Glu Glu Lys
            340                 345                 350
Asn Gln Val Leu Val Arg Asp Val Glu Thr Gly Glu Leu Arg Pro Gln
        355                 360                 365
Arg Val Val Lys Leu Gly Ser Val Arg Ser Lys Gly Val Val Ala Pro
    370                 375                 380
Leu Thr Arg Glu Gly Thr Ile Val Val Asn Ser Val Ala Ala Ser Cys
385                 390                 395                 400
Tyr Ala Val Ile Asn Ser Gln Ser Leu Ala His Trp Gly Leu Ala Pro
                405                 410                 415
Met Arg Leu Leu Ser Thr Leu Glu Ala Trp Leu Pro Ala Lys Glu Gln
            420                 425                 430
Leu His Ser Ser Pro Lys Val Val Ser Ser Ala Gln Gln Asn Gly
        435                 440                 445
Ile His Trp Tyr Ala Asn Ala Leu Tyr Lys Val Lys Asp Tyr Val Leu
    450                 455                 460
Pro Gln Ser Trp Arg His Asp
465                 470
```

<210> SEQ ID NO 19
<211> LENGTH: 221
<212> TYPE: PRT
<213> ORGANISM: Artificial Sequence
<220> FEATURE:
<223> OTHER INFORMATION: Description of Artificial Sequence: degenerate
      polypeptide sequence
<220> FEATURE:
<222> LOCATION: 7
<223> OTHER INFORMATION: Gly, Ala, Val, Leu, Ile, Phe, Tyr or Trp
<220> FEATURE:
<222> LOCATION: 9
<223> OTHER INFORMATION: Arg, His or Lys
<220> FEATURE:
<222> LOCATION: 44
<223> OTHER INFORMATION: Gly, Ala, Val, Leu, Ile, Ser or Thr
<220> FEATURE:
<222> LOCATION: 85
<223> OTHER INFORMATION: Gly, Ala, Val, Leu, Ile, Ser or Thr
<220> FEATURE:
<222> LOCATION: 93
<223> OTHER INFORMATION: Lys, Arg, His, Asn or Gln
<220> FEATURE:
<222> LOCATION: 98
<223> OTHER INFORMATION: Lys, Arg or His
<220> FEATURE:
<222> LOCATION: 112
<223> OTHER INFORMATION: Ser, Thr, Tyr, Trp or Phe
<220> FEATURE:
<222> LOCATION: 132
<223> OTHER INFORMATION: Lys, Arg or His
<220> FEATURE:
<222> LOCATION: 137
<223> OTHER INFORMATION: Met, Cys, Ser or Thr
<220> FEATURE:
<222> LOCATION: 139
<223> OTHER INFORMATION: Gly, Ala, Val, Leu, Ile, Ser or Thr
<220> FEATURE:

```
<222> LOCATION: 181
<223> OTHER INFORMATION: Leu, Val, Met, Thr or Ser
<220> FEATURE:
<222> LOCATION: 183
<223> OTHER INFORMATION: His, Phe, Tyr, Ser, Thr, Met or Cys
<220> FEATURE:
<222> LOCATION: 185
<223> OTHER INFORMATION: Gln, Asn, Glu, or Asp
<220> FEATURE:
<222> LOCATION: 186
<223> OTHER INFORMATION: His, Phe, Tyr, Thr, Gln, Asn, Glu or Asp
<220> FEATURE:
<222> LOCATION: 189
<223> OTHER INFORMATION: Gln, Asn, Glu, Asp, Thr, Ser, Met or Cys
<220> FEATURE:
<222> LOCATION: 191
<223> OTHER INFORMATION: Ala, Gly, Cys, Leu, Val or Met
<220> FEATURE:
<222> LOCATION: 196
<223> OTHER INFORMATION: Arg, Lys, Met, Ile, Asn, Asp, Glu, Gln, Ser,
      Thr or Cys
<220> FEATURE:
<222> LOCATION: 200
<223> OTHER INFORMATION: Arg, Lys, Met or Ile
<220> FEATURE:
<222> LOCATION: 206
<223> OTHER INFORMATION: Ala, Gly, Cys, Asp, Glu, Gln, Asn, Ser, Thr or
      Met
<220> FEATURE:
<222> LOCATION: 207
<223> OTHER INFORMATION: Ala, Gly, Cys, Asp, Asn, Glu or Gln
<220> FEATURE:
<222> LOCATION: 209
<223> OTHER INFORMATION: Arg, Lys, Met, Ile, Asn, Asp, Glu or Gln
<220> FEATURE:
<222> LOCATION: 211
<223> OTHER INFORMATION: Leu, Val, Met or Ile
<220> FEATURE:
<222> LOCATION: 212
<223> OTHER INFORMATION: Phe, Tyr, Thr, His or Trp
<220> FEATURE:
<222> LOCATION: 216
<223> OTHER INFORMATION: Ile, Val, Leu or Met
<220> FEATURE:
<222> LOCATION: 217
<223> OTHER INFORMATION: Met, Cys, Ile, Leu, Val, Thr or Ser
<220> FEATURE:
<222> LOCATION: 219
<223> OTHER INFORMATION: Leu, Val, Met, Thr or Ser
<220> FEATURE:
<223> OTHER INFORMATION: each Xaa may also be any amino acid.

<400> SEQUENCE: 19

Cys Gly Pro Gly Arg Gly Xaa Gly Xaa Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Xaa Arg Asn Ser Glu
         35                  40                  45

Arg Phe Lys Glu Leu Thr Pro Asn Tyr Asn Pro Asp Ile Ile Phe Lys
     50                  55                  60

Asp Glu Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
        100                 105                 110

Glu Glu Ser Leu His Tyr Glu Gly Arg Ala Val Asp Ile Thr Thr Ser
            115                 120                 125

Asp Arg Asp Xaa Ser Lys Tyr Gly Xaa Leu Xaa Arg Leu Ala Val Glu
```

```
                130                 135                 140
Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
                180                 185                 190

Lys Asp Leu Xaa Pro Gly Asp Xaa Val Leu Ala Ala Asp Xaa Xaa Gly
            195                 200                 205

Xaa Leu Xaa Xaa Ser Asp Phe Xaa Xaa Phe Xaa Asp Arg
    210                 215                 220
```

<210> SEQ ID NO 20
<211> LENGTH: 167
<212> TYPE: PRT
<213> ORGANISM: Artificial Sequence
<220> FEATURE:
<223> OTHER INFORMATION: Description of Artificial Sequence: degenerate
      polypeptide sequence
<220> FEATURE:
<222> LOCATION: 7
<223> OTHER INFORMATION: Gly, Ala, Val, Leu, Ile, Pro, Phe or Tyr
<220> FEATURE:
<222> LOCATION: 8
<223> OTHER INFORMATION: Gly, Ala, Val, Leu or Ile
<220> FEATURE:
<222> LOCATION: 9
<223> OTHER INFORMATION: Gly, Ala, Val, Leu, Ile, Lys, His or Arg
<220> FEATURE:
<222> LOCATION: 12
<223> OTHER INFORMATION: Lys, Arg or His
<220> FEATURE:
<222> LOCATION: 13
<223> OTHER INFORMATION: Phe, Trp, Tyr or an amino acid gap
<220> FEATURE:
<222> LOCATION: 14
<223> OTHER INFORMATION: Gly, Ala, Val, Leu, Ile or an amino acid gap
<220> FEATURE:
<222> LOCATION: 17
<223> OTHER INFORMATION: Asn, Gln, His, Arg or Lys
<220> FEATURE:
<222> LOCATION: 19
<223> OTHER INFORMATION: Gly, Ala, Val, Leu, Ile, Ser or Thr
<220> FEATURE:
<222> LOCATION: 22
<223> OTHER INFORMATION: Gly, Ala, Val, Leu, Ile, Ser or Thr
<220> FEATURE:
<222> LOCATION: 27
<223> OTHER INFORMATION: Gly, Ala, Val, Leu, Ile, Ser or Thr
<220> FEATURE:
<222> LOCATION: 29
<223> OTHER INFORMATION: Ser, Thr, Gln or Asn
<220> FEATURE:
<222> LOCATION: 30
<223> OTHER INFORMATION: Met, Cys, Gly, Ala, Val, Leu, Ile, Ser or Thr
<220> FEATURE:
<222> LOCATION: 31
<223> OTHER INFORMATION: Gly, Ala, Val, Leu, Ile or Pro
<220> FEATURE:
<222> LOCATION: 33
<223> OTHER INFORMATION: Arg, His or Lys
<220> FEATURE:
<222> LOCATION: 40
<223> OTHER INFORMATION: Gly, Ala, Val, Leu, Ile, Pro, Arg, His or Lys
<220> FEATURE:
<222> LOCATION: 41
<223> OTHER INFORMATION: Gly, Ala, Val, Leu, Ile, Phe or Tyr
<220> FEATURE:
<222> LOCATION: 44
<223> OTHER INFORMATION: Arg, His or Lys
<220> FEATURE:
<222> LOCATION: 45
<223> OTHER INFORMATION: Gly, Ala, Val, Leu, Ile, Ser or Thr -continued

```
<220> FEATURE:
<222> LOCATION: 46
<223> OTHER INFORMATION: Thr or Ser
<220> FEATURE:
<222> LOCATION: 48
<223> OTHER INFORMATION: Gly, Ala, Val, Leu, Ile, Asn or Gln
<220> FEATURE:
<222> LOCATION: 53
<223> OTHER INFORMATION: Arg, His or Lys
<220> FEATURE:
<222> LOCATION: 54
<223> OTHER INFORMATION: Asp or Glu
<220> FEATURE:
<222> LOCATION: 71
<223> OTHER INFORMATION: Ser or Thr
<220> FEATURE:
<222> LOCATION: 79
<223> OTHER INFORMATION: Glu, Asp, Gln or Asn
<220> FEATURE:
<222> LOCATION: 83
<223> OTHER INFORMATION: Glu or Asp
<220> FEATURE:
<222> LOCATION: 84
<223> OTHER INFORMATION: Arg, His or Lys
<220> FEATURE:
<222> LOCATION: 85
<223> OTHER INFORMATION: Gly, Ala, Val, Leu or Ile
<220> FEATURE:
<222> LOCATION: 87
<223> OTHER INFORMATION: Gly, Ala, Val, Leu, Ile, Thr or Ser
<220> FEATURE:
<222> LOCATION: 95
<223> OTHER INFORMATION: Met, Cys, Gln, Asn, Arg, Lys or His
<220> FEATURE:
<222> LOCATION: 100
<223> OTHER INFORMATION: Arg, His or Lys
<220> FEATURE:
<222> LOCATION: 107
<223> OTHER INFORMATION: Trp, Phe, Tyr, Arg, His or Lys
<220> FEATURE:
<222> LOCATION: 114
<223> OTHER INFORMATION: Gly, Ala, Val, Leu, Ile, Ser, Thr, Tyr or Phe
<220> FEATURE:
<222> LOCATION: 115
<223> OTHER INFORMATION: Gln, Asn, Asp or Glu
<220> FEATURE:
<222> LOCATION: 116
<223> OTHER INFORMATION: Asp or Glu
<220> FEATURE:
<222> LOCATION: 125
<223> OTHER INFORMATION: Gly, Ala, Val, Leu, or Ile
<220> FEATURE:
<222> LOCATION: 134
<223> OTHER INFORMATION: Arg, His or Lys
<220> FEATURE:
<222> LOCATION: 135
<223> OTHER INFORMATION: Asn, Gln, Thr or Ser
<220> FEATURE:
<222> LOCATION: 139
<223> OTHER INFORMATION: Gly, Ala, Val, Leu, Ile, Ser, Thr, Met or Cys
<220> FEATURE:
<222> LOCATION: 141
<223> OTHER INFORMATION: Gly, Ala, Val, Leu, Ile, Thr or Ser
<220> FEATURE:
<222> LOCATION: 157
<223> OTHER INFORMATION: Arg, His or Lys
<220> FEATURE:
<222> LOCATION: 158
<223> OTHER INFORMATION: Asn, Gln, Gly, Ala, Val, Leu or Ile
<220> FEATURE:
<222> LOCATION: 160
<223> OTHER INFORMATION: Gly, Ala, Val, Leu or Ile
<220> FEATURE:
<222> LOCATION: 162
<223> OTHER INFORMATION: Gly, Ala, Val, Leu, Ile, Ser, Thr or Cys
<220> FEATURE:
<222> LOCATION: 166
<223> OTHER INFORMATION: Gly, Ala, Val, Leu, Ile, Thr or Ser
<220> FEATURE:
```

-continued

```
<222> LOCATION: 167
<223> OTHER INFORMATION: Asp or Glu

<400> SEQUENCE: 20

Cys Gly Pro Gly Arg Gly Xaa Xaa Xaa Arg Arg Xaa Xaa Xaa Pro Lys
 1               5                  10                  15

Xaa Leu Xaa Pro Leu Xaa Tyr Lys Gln Phe Xaa Pro Xaa Xaa Xaa Glu
                20                  25                  30

Xaa Thr Leu Gly Ala Ser Gly Xaa Xaa Glu Gly Xaa Xaa Xaa Arg Xaa
            35                  40                  45

Ser Glu Arg Phe Xaa Xaa Leu Thr Pro Asn Tyr Asn Pro Asp Ile Ile
 50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
                85                  90                  95

Pro Gly Val Xaa Leu Arg Val Thr Glu Gly Xaa Asp Glu Asp Gly His
                100                 105                 110

His Xaa Xaa Xaa Ser Leu His Tyr Glu Gly Arg Ala Xaa Asp Ile Thr
        115                 120                 125

Thr Ser Asp Arg Asp Xaa Xaa Lys Tyr Gly Xaa Leu Xaa Arg Leu Ala
130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
                165

<210> SEQ ID NO 21
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 21
gcgcgcttcg aagcgaggca gccagcgagg gagagagcga gcgggcgagc cggagcgagg    60
aaatcgatgc gcgc                                                     74

<210> SEQ ID NO 22
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 22
gcgcgcagat ctgggaaagc gcaagagaga gcgcacacgc acacacccgc cgcgcgcact    60
cgggatccgc gcgc                                                     74

<210> SEQ ID NO 23
<211> LENGTH: 996
<212> TYPE: DNA
<213> ORGANISM: Artificial Sequence
<220> FEATURE:
<223> OTHER INFORMATION: Description of Artificial Sequence: gene
      activation construct

<400> SEQUENCE: 23
cgaagcgagg cagccagcga gggagagagc gagcgggcga gccggagcga ggaaatcgaa    60
```

-continued

```
ggttcgaatc cttcccccac caccatcact ttcaaaagtc cgaaagaatc tgctccctgc      120
ttgtgtgttg gaggtcgctg agtagtgcgc gagtaaaatt taagctacaa caaggcaagg      180
cttgaccgac aattgcatga agaatctgct tagggttagg cgttttgcgc tgcttcgcga      240
tgtacgggcc agatatacgc gttgacattg attattgact agttattaat agtaatcaat      300 tacgggtca ttagttcata gcccatatat ggagttccgc gttacataac ttacggtaaa       360
tggcccgcct ggctgaccgc ccaacgaccc ccgcccattg acgtcaataa tgacgtatgt      420
tcccatagta acgccaatag ggactttcca ttgacgtcaa tgggtggact atttacggta      480
aactgcccac ttggcagtac atcaagtgta tcatatgcca agtacgcccc ctattgacgt      540
caatgacggt aaatggcccg cctggcatta tgcccagtac atgaccttat gggactttcc      600
tacttggcag tacatctacg tattagtcat cgctattacc atggtgatgc ggttttggca      660
gtacatcaat gggcgtggat agcggtttga ctcacgggga tttccaagtc tccacccat      720 tgacgtcaat gggagtttgt tttggcacca aaatcaacgg gactttccaa aatgtcgtaa      780
caactccgcc ccattgacgc aaatgggcgg taggcgtgta cggtgggagg tctatataag      840
cagagctctc tggctaacta gagaacccac tgcttactgg cttatcgaaa ttaatacgac      900
tcactatagg gagacccaag cttggtaccg agctcggatc gatctgggaa agcgcaagag      960
agagcgcaca cgcacacacc cgccgcgcgc actcgg                                996
```

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: antisense
      construct

<400> SEQUENCE: 24
gtcctggcgc cgccgccgcc gtcgcc      26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: antisense
      construct

<400> SEQUENCE: 25
ttccgatgac cggcctttcg cggtga      26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: antisense
      construct

<400> SEQUENCE: 26
gtgcacggaa aggtgcaggc cacact      26

NEUROPROTECTIVE METHODS AND REAGENTS

This application is a continuation-in-part of U.S. patent application Ser. No. 08/883,656, filed Jun. 27, 1997, abandoned incorporated herein by reference in its entirety.

BACKGROUND OF THE INVENTION

Stroke kills more than 150,000 people annually and accounts for about one of every 15 U.S. deaths. It is presently the third largest cause of death, ranking behind diseases of the heart and cancer, according to the National Center for Health Statistics.

On average, someone suffers a stroke in the United States every minute; every 3.4 minutes someone dies of a stroke. Based on the Framingham Heart Study, approximately 500,000 people suffer a new or recurrent brain attack each year. Approximately 3,890,000 stroke survivors are alive today. From 1984 to 1994, the death rate from stroke declined 19.8 percent, but the actual number of deaths from brain attack rose slightly.

Stroke is the leading cause of serious, long-term disability in the United States. Stroke accounts for half of all patients hospitalized for acute neurological disease. In 1991–92 one million Americans age 15 and older had disabilities resulting from stroke. According to the Framingham Heart Study, 31 percent of brain attack survivors needed help caring for themselves; 20 percent needed help walking; and 71 percent had an impaired ability to work when examined an average of seven years later. Sixteen percent had to be institutionalized. About 31 percent of people who have an initial stroke die within a year. This percentage is higher among people older than age 65. About two-thirds of men and women who have a brain attack die within 12 years; long-term survivorship is worse in men than in women. 407,000 males and 478,000 females were discharged from hospitals in 1994 after having a stroke.

Stroke is defined as a sudden impairment of body functions caused by a disruption in, e.g., the supply of blood to the brain. For instance, a stroke occurs when a blood vessel bringing oxygen and nutrients to the brain is interrupted by any method including low blood pressure, clogging by atherosclerotic plaque, a blood clot, or some other particle, or when a blood vessel bursts.

Because of the blockage or rupture, part of the brain fails to get the blood flow that it requires. Brain tissue that receives an inadequate supply of blood is said to be ischemic. Deprived of oxygen and nutrients, nerve cells and other cell types within the brain begin to fail, creating an infarct (an area of cell death, or necrosis). As nerve cells (neurons) fail and die, the part of the body controlled by those neurons cannot function either. The devastating effects of ischemia are often permanent because brain tissue has very limited repair capabilities and lost neurons are not usually replaced.

Cerebral ischemia may be incomplete (blood flow is reduced but not entirely cut off), complete (total loss of tissue perfusion), transient or permanent. If ischemia is incomplete and persists for no more than ten to fifteen minutes, neural death might not occur. More prolonged or complete ischemia results in infarction. Depending on the site and extent of the infarction, mild to severe neurological disability or death will follow. Thus, the chain of causality leading to neurological deficit in stroke has two principal components: loss of blood supply, and cell damage and death.

Thrombosis is the blockage of an artery by a large deposit that usually results from the combination of atherosclerosis and blood clotting. Thrombotic stroke (also called cerebral thrombosis) results when a deposit in a brain or neck artery reaches occlusive proportions. Most strokes are of this type.

Embolism is the blockage of an artery or vein by an embolus. Emboli are often small pieces of blood clot that break off from larger clots. Embolic stroke (also called cerebral embolism) occurs when an embolus is carried in the bloodstream to a brain or neck artery. If the embolus reaches an artery that is too small for it to pass through, it plugs the artery and cuts off the blood supply to downstream tissues. Embolic stroke is the clinical expression of this event.

To a modest extent, the brain is protected against cerebral ischemia by compensatory mechanisms that include: collateral circulation (overlapping local blood supplies), and arteriolar auto-regulation (local smooth muscle control of blood flow in the smallest arterial channels). If compensatory mechanisms operate efficiently, slightly diminished cerebral blood flow produces neither tissue ischemia nor abnormal signs and symptoms. Usually, such mechanisms must act within minutes to restore blood flow if permanent infarction damage is to be avoided or reduced. Arteriolar auto-regulation works by shunting blood from noncritical regions to infarct zones.

Even in the face of systemic hypotension, auto-regulation may be sufficient to adjust the circulation and thereby preserve the vitality and function of brain tissue. Alternatively, ischemia may be sufficiently prolonged and compensatory mechanisms sufficiently inadequate that a catastrophic stroke results. With these as the extremes, the gradation of ischemic stroke are described below.

A transient ischemic attack (TIA) is conventionally described as a loss of neurologic function caused by ischemia, abrupt in onset, persisting for less than 24 hours, and clearing without residual signs. Most TIAs last only a few minutes. However, neurologic disability may persist for more than 24 hours before clearing. Such an event is called a reversible ischemic neurological disability (RIND).

An ischemic event that is sufficiently severe to cause persistent disability but that is short of a calamitous stroke, is called a partial nonprogressing stroke (PNS). The penultimate ischemic event, a completed stroke, produces major functional loss. The ultimate ischemic insult is death.

Focal cerebral ischemia must be distinguished from global cerebral hypoxia. In cerebral hypoxia the oxygen supply to the brain is diminished even though blood flow and blood pressure may be normal. Discriminating between diagnoses of patients with acute neurological deficit is critical because patient management takes disparate paths.

There are generally distinct clinical outcomes in stroke versus cerebral hypoxia, although both sets of patients may suffer death or permanent damage. Hypoxia patients who survive past an acute life-threatening period usually show few immediate symptoms of long term damage. Instead, clinical manifestations such as mental deterioration, urinary and fecal incontinence, gait and speech disturbances, tremor and weakness are delayed for periods that may vary from days to weeks. However, as in stroke, progressive loss of neurons due to oxygen deprivation is believed to be a factor in such detrimental effects of hypoxia.

It is an objective of the present application to provide new drugs for treatment and prophylaxis of cerebral ischemia, such as stroke.

It is also an objective of the present application to provide new drugs for treatment and prophylaxis of cerebral hypoxia.

SUMMARY OF THE INVENTION

One aspect of the present application relates to a method for limiting damage to neuronal cells by ischemic or hypoxic conditions, e.g., such as may be manifest by a reduction in brain infarct volume, by administering to an individual a hedgehog therapeutic or ptc therapeutic in an amount effective for reducing cerebral infarct volume relative to the absence of administeration of the hedgehog therapeutic or ptc therapeutic.

In other embodiments, the subject method can be used for protecting cerebral tissue of a mammal against the repercussions of ischemia; for treating cerebral infarctions; for treating cerebral ischemia; for treatment of stroke; and/or for treating transient ischemia attacks. In embodiments wherein the patient is treated with a ptc therapeutic, such therapeutics are preferably small organic molecules which mimic hedgehog effects on patched-mediated signals.

Wherein the subject method is carried out using a hedgehog therapeutic, the hedgehog therapeutic preferably a polypeptide including a hedgehog portion comprising at least a bioactive extracellular portion of a hedgehog protein, e.g., the hedgehog portion includes at least 50, 100 or 150 amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In preferred embodiments, the hedgehog portion has an amino acid sequence at least 60, 75, 85, or 95 percent identical with a hedgehog protein of any of SEQ ID Nos. 10–18, though sequences identical to those sequence listing entries are also contemplated as useful in the present method. The hedgehog portion can be encoded by a nucleic acid which hybridizes under stringent conditions to a nucleic acid sequence of any of SEQ ID Nos. 1–9, e.g., the hedgehog portion can be encoded by a vertebrate hedgehog gene, especially a human hedgehog gene.

In other embodiments, the subject method can be carried out by administering a gene activation construct, wherein the gene activation construct is designed to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent.

Where the subject method is carried out using a ptc therapeutic, the therapeutic can be, e.g., a molecule which binds to patched and mimics hedgehog-mediated patched signal transduction. For instance, the binding of the therapeutic to patched may result in upregulation of patched and/or gli expression.

In other embodiments, the ptc therapeutic mimics hedgehog-mediated patched signal transduction by altering the localization, protein-protein binding and/or enzymatic activity of an intracellular protein involved in a patched signal pathway.

In a preferred embodiment, the ptc therapeutic is a small organic molecule, e.g., less than 5 kd, more preferably less than 2.5 kd. For instance, the present invention contemplates the use of small organic molecules which interact with neuronal cells to mimic hedgehog-mediated patched signal transduction.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

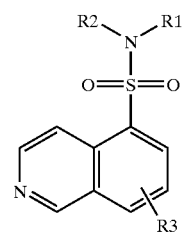

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-O$-lower alkyl, $-(CH_2)_m-O$-lower alkenyl; $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

Exemplary PKA inhibitors of this class include N-[2-((p-bromocinnamyl)amino)ethyl]-5-isoquinoline-sulfonamide and 1-(5-isoquinolinesulfonyl)-2-methylpiperazine. Other PKA inhibitors which can be used in the subject method include KT5720; and PKA Heat Stable Inhibitor (isoform α).

In yet other embodiments of the present invention, the ptc therapeutic alters the level of expression of a hedgehog protein, a patched protein or another protein involved in the intracellular signal transduction pathway of patched. In this regard, the ptc therapeutic can be an antisense construct which inhibits the expression of a protein which is involved in the signal transduction pathway of patched and the expression of which antagonizes hedgehog-mediated signals. For example, the antisense molecule can be one which hyridizes to a patched transcript or genomic sequence, such as 5'-GTCCTGGCGCCGCCGCCGCCGTCGCC, 5'-TTCCGATGACCGGCCTTTCGCGGTGA or 5'-GTGCACGGAAAGGTGCAGGCCACACT (SEQ ID NOS: 24–26).

In yet other embodiments, the subject method can be carried out with a gene activation construct, which construct recombines with a genomic hedgehog gene of the patient, e.g., to form a chimeric gene, providing a heterologous transcriptional regulatory sequence operatively linked to a coding sequence of the hedgehog gene. The transcriptional regulatory sequence can provide for constitutive or inducible expression of the hedgehog gene.

The subject method can be used as part of a treatment for stroke, e.g., thrombotic stroke and/or embolic stroke.

The subject method can also be used to treat hypoxic conditions which otherwise result in cerebral hypoxia.

The subject method can be used prophylactically or as an ipso facto treatment. It can be used to treat patients who are hypotensive.

The subject method can also be used as part of a therapy including administering one or more of an anticoagulant, an antiplatelet agent, a thrombin inhibitor, and/or a thrombolytic agent, and/or in conjunction with vascular surgery, e.g., carotid endarterectomy.

In preferred embodiments, the subject method results in at least a 25%, 50%, 70%, 75%, or 90% reduction in cerebral infarct volumes relative to the absence of treatment with the therapeutic, e.g., as measured in a stroke model such as the MCAO model.

DETAILED DESCRIPTION OF THE INVENTION

Figure 1:
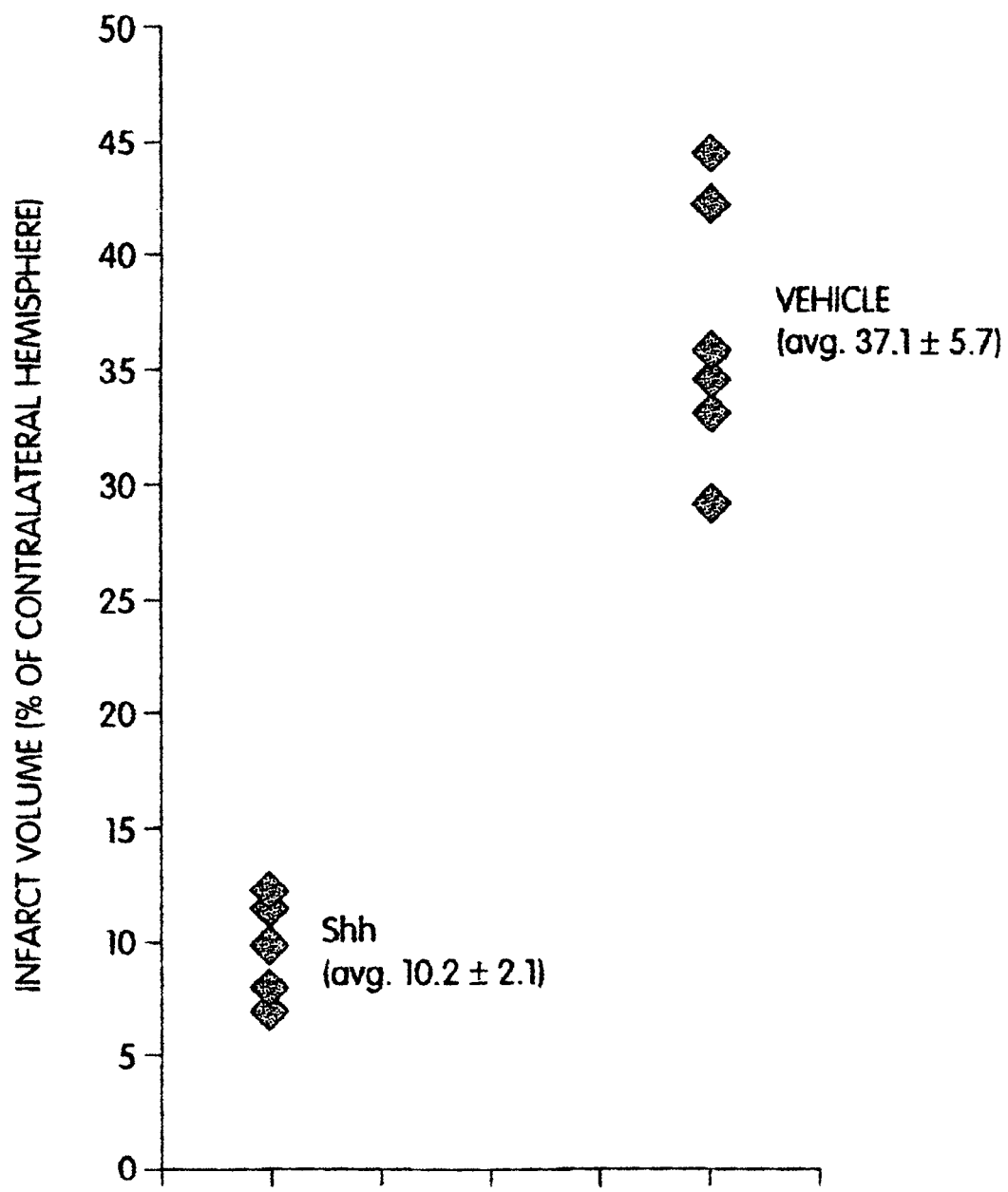
FIG. 1 is a graph demonstrating the effect of systemic hedgehog treatment on cerebral infarction volume in rat models of middle cerebral artery occlusion.

Stroke occurs when the flow of oxygen and nutrients to the brain is inhibited/interrupted due to any cause. Thus, in certain indications, stroke is a form interrupted of cardiovascular disease that affects the arteries of the central nervous system. For example, a stroke occurs when a blood vessel bringing oxygen and nutrients to the brain bursts or is clogged by a blood clot or some other particle. Because of this rupture or blockage, part of the brain doesn't get the flow of blood it needs. Deprived of oxygen, nerve cells in the affected area of the brain can't function and die within minutes. Depending on the part of the brain affected by the brain attack/stroke, there may be loss of normal function. Strokes are the third most common cause of death in United States. Stroke is the most common cause of disability of all conditions in adults.

In terms of treatment, once a patient experiences symptoms of a transient ischemic attack, the goal of therapy is prevention of stroke. If a stroke occurs, the goal of therapy changes to the limiting of damage. Preventing stroke and limiting the damage of stroke are currently carried out in the art through medication or surgery. In both cases, the treatment involves reducing or removing blocks, building up in blood vessels and preventing further cell death about neuronal populations. These treatments include the use of (a) anticoagulants, (b) antiplatelet agents, and (c) vascular surgery. For instance, anticoagulation drug therapy inhibits the coagulation process. Heparin, which inhibits enzymes and platelets-that cause clots, is used in acute settings. For long term prevention, warfarin offers anticoagulation by stopping production of Vitamin K dependent coagulation factors. With both drugs, there runs a risk of hemorrhage and is only used for ischemic strokes. Strokes involving certain areas also do not warrant this therapy. Another therapy known in the art, antiplatelet therapy with aspirin, provides one of the most important preventive tools available. At low daily doses, aspirin has been shown to reduce the incidence of stroke. Specifically, low doses of aspirin block the production of a chemical called thromboxane. Thromboxane's function is to activate platelets to bind together and thus form blood clots. Finally, carotid endarterectomy is the surgical procedure where the plaque at the origin of the carotid artery is removed. This is the treatment of choice of patients with TIA's caused by embolism, low flow, and with minor strokes due to narrowing greater than 70% of the internal carotid.

I. Overview

The present application is directed to compositions and methods for the prevention and treatment of ischemic injury to the brain, such as resulting from stroke. The invention derives, at least in part, from the observation of a protective effect by the so called "hedgehog" proteins on animal stroke models. Briefly, as described in the appended examples, we investigated the neuroprotective potential of hedgehog proteins in a rat model of focal cerebral ischemia that used permanent occlusion of the middle cerebral artery. Intravenous infusion of vehicle (control) or Shh (sonic hedgehog) was administered for 3 hours beginning 30 minutes after occlusion, and resulted in about a 70 percent reduction in total infarct size (P=0.0039), relative to the control, when examined 24 hours post-occlusion. Measurements of arterial blood pressure, blood gases, glucose, hematocrit and osmolality revealed no difference among vehicle- and Shh-treated animals. These results show that the intravenous hedgehog protein reduces neuronal damage due to stroke. There was no apparent cytotoxicity associated with administration of the hedgehog polypeptide.

These results, in comparison to neuroprotective agents described in the art, suggest an unexpectedly good neuroprotective activity for hedgehog in the treatment of stroke. For example, the non-competitive antagonist of the NMDA receptor, MK-801, was typically reported to produce less than a 50% reduction in infarct volume. Work on MK-801 was halted because of significant safety concerns, mostly related to vacuolization seen in neurons of animal models. Moreover, MK-801 has a relatively short therapeutic window and must be given within a few hours of the ischemic attack.

Another neuroprotective agent presently being investigated for use in the treatment of stroke is basic fibroblast growth factor (bFGF). In one study, (Tatlisumak et al. (1996) *Stroke* 27:2292), bFGF (45 $\mu$g/kg/hr) or vehicle was infused intravenously for three hours beginning 30 minutes after permanent middle cerebral artery occlusion by intraluminal suture in mature Sprague-Dawley rats. After 24 hours, neurological deficit and infract volume were significantly improved (approximately 50% reduction in infarct volume) in the FGF group. Autoradiography following intravenous administration of radiolabeled bFGF showed that labeled FGF (confirmed by immunoprecipitation) crossed the damaged blood brain barrier to enter the ischemic, but not the non-ischemic hemisphere.

A second model (Jiang et al. (1995) *Stroke* 26:1–40), utilized mature Wistar rats which underwent temporary occlusion of the middle cerebral artery by intra-arterial suture for two hours. At the time of reperfusion either bFGF (45 $\mu$g/kg/hr) or vehicle were infused intravenously over three hours. At seven days after ischemia, infarct volume was significantly reduced in the bFGF treated animals (approximately 40% reduction in infarct volume), and only the bFGF treated animals regained their weight after surgery.

In one aspect, the present invention provides pharmaceutical preparations and methods for preventing/treating cerebral ischemia and the like utilizing, as an active ingredient, a hedgehog polypeptide or a mimetic thereof.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

However, without wishing to be bound by any particular theory, the reduction in infarct size in the present studies may be due at least in part to the ability of hedgehog proteins to antagonize (directly or indirectly) patched-mediated regulation of gene expression and other physiological effects mediated by the patched gene. The patched gene product, a cell surface protein, is understood to signal through a pathway which regulates transcription of a variety of genes involved in neuronal cell development. In the CNS and other tissue, the introduction of hedgehog relieves (derepresses) this inhibition conferred by patched, allowing expression of particular gene programs.

Accordingly, the present invention contemplates the use of other agents which are capable of mimicking the effect of the hedgehog protein on patched signalling, e.g., as may be identified from the drug screening assays described below.

II. Definitions

For convience, certain terms employed in the specfication, examples, and appended claims are collected here.

A "stroke" is a sudden loss of function caused by a cutoff in the blood supply to the brain. Stroke presents with different levels of severity ranging from "transient ischemic attack" or "TIA" (no permanent disability), to "partial nonprogressing stroke" (persistent but no calamitous damage), to "complete stroke" (permanent, calamitous neurological deficit). Ischemia (diminished or stopped blood flow) and infarction (cell damage and death within the zone of ischemia) are the pathologic processes in stroke that lead to neurologic deficits.

"Ischemic stroke" is caused by an obstruction of blood vessels supplying the brain. The primary subcategories of ischemic stroke are thrombotic stroke, embolic stroke and lacunar infarctions.

"Hemorrhagic stroke" is caused by the rupture of blood vessels supplying the brain. The primary subcategories of hemorrhagic stroke are subarachnoid hemorrhage (SAH) and intracerebral hemorrhage (ICH).

The term "ischemic damage" refers to a reduction in the biological capability of a neuronal cell, including cell death, induced by a reduced blood flow, or an otherwise reduced level of oxygen to the affected neuronal cells, whether it be the result of ischemic stroke, hemmorrhagic stroke, hypoxia or the like.

The term "hedgehog therapeutic" refers to various forms of hedgehog polypeptides, as well as peptidomimetics, which are neuroprotective for neuronal cells, and in particular, enhance the survival of neurons under ischemic and/or hypoxic conditions. These include naturally occurring forms of hedgehog proteins, as well as modified or mutant forms generated by molecular biological techniques, chemical synthesis, etc. While in preferred embodiments the hedgehog polypeptide is derived from a vertebrate homolog, cross-species activity reported in the literature supports the use of hedgehog polypeptides from invertebrate organisms as well. Naturally and non-naturally occurring hedgehog therapeutics referred to herein as "agonists" mimic or potentiate (collectively "agonize") the effects of a naturally occurring hedgehog protein as a neuroprotective agent. In addition, the term "hedgehog therapeutic" includes molecules which can activate expression of an endogenous hedgehog gene. The term also includes gene therapy constructs for causing expression of hedgehog polypeptides in vivo, as for example, expression constructs encoding recombinant hedgehog polypeptides as well as trans-activation constructs for altering the regulatory sequences of an endogenous hedgehog gene by homologous recombination.

In particular, the term "hedgehog polypeptide" encompasses hedgehog proteins and peptidyl fragments thereof.

As used herein the term "bioactive fragment", with reference to portions of hedgehog proteins, refers to a fragment of a full-length hedgehog protein, wherein the fragment specifically agonizes neuroprotective events mediated by wild-type hedgehog proteins. The hedgehog bioactive fragment preferably is a soluble extracellular portion of a hedgehog protein, where solubility is with reference to physiologically compatible solutions. Exemplary bioactive fragments are described in PCT publications WO 95/18856 and WO 96/17924.

The term "ptc therapeutic" refers to agents which mimic the effect of naturally occurring hedgehog proteins on patched signalling. The ptc therapeutic can be, e.g., a peptide, a nucleic acid, a carbohydrate, a small organic molecule, or natural product extract (or fraction thereof).

A "patient" or "subject" to be treated by the subject method is a mammals, including a human.

A "therapeutically effective amount" of, e.g., a hedgehog or ptc therapeutic, with respect to the subject method of treatment, refers to an amount of the therapeutic (in a preparation) which when applied as part of a desired dosage regimen causes a decrease in ischemia- and/or hypoxia-induced neuronal cell death (i.e., a reduction in the volume/size of a cerebral infarct caused thereby) according to clinically acceptable standards for the treatment or prevention of those disorder.

By "protection from damage to neural tissue" it is meant reduction in the total stroke volume and/or infarct volume resulting from, e.g., ischemic or hypoxic conditions, preferably as manifested by less neurological and/or cognitive deficits.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with an AR sequence of the present invention.

The term "corresponds to", when referring to a particular polypeptide or nucleic acid sequence is meant to indicate that the sequence of interest is identical or homologous to the reference sequence to which it is said to correspond.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n\text{-}(hh)_m\text{-}(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

As used herein, the term "vector" refers to a nucleic acid molecule capable of transporting another nucleic acid to which it has been linked. The term "expression vector" includes plasmids, cosmids or phages capable of synthesizing, for example, the subject hedgehog polypeptides encoded by the respective recombinant gene carried by the vector. Preferred vectors are those capable of autonomous replication and/or expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein (or antisense) coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

The term "operably linked" refers to the arrangement of a transcriptional regulatory element relative to another transcribable nucleic acid sequence, such that the transcriptional regulatory element can regulate the rate of transcription from the transcribable sequence(s).

III. Exemplary Applications of Method and Compositions

Central nervous system tissue is particularly vulnerable to damage caused by ischemic conditions. The subject method has wide applicability to the treatment or prophylaxis of ischemic or hypoxic damage marked by neuronal cell death. The instant treatment can be used to treat or prevent injury or disease to brain tissue resulting from ischemia, e.g., as caused from insufficient oxygen. The types of ischemia for which the subject method can be used as part of a treatment include, but are not limited to those which may last for only transient periods of time to those which may last for lengthy durations, as in stroke. In the regard, the subject method is useful for treatment and prevention of injury to the brain and spinal cord and edema due to head trauma, spinal trauma, stroke, hypotension, arrested breathing, cardiac arrest, Rey's syndrome, cerebral thrombosis, embolism, hemorrhage or tumors, encephalomyelitis, hydroencephalitis, and operative and postoperative brain injury.

In general, the method can be characterized as including a step of administering to an animal an amount of a ptc or hedgehog therapeutic effective to enhance the survival of neuronal cells under such ischemic or hypoxic conditions. The mode of administration and dosage regimens will vary depending on the severity of the ischemic or hypoxic attack, e.g., the dosage may be altered as between a transient ischemic attack, a partial nonprogressing stroke, and a complete stroke. In preferred embodiments, the ptc or hedgehog therapeutic is administered systemically initially (i.e., while the blood brain barrier is disrupted), then locally for medium to long term care.

When used to treat stroke, the clinician should not only define the level of stroke severity, but also the "pace" or "tempo" of the illness. This is because the pace of progression helps to dictate the urgency for evaluation and treatment. A patient who suffers a TIA in the morning has a higher risk for stroke in the afternoon than a patient who suffered a single TIA a month earlier. Where the risk of stroke remains high, the subject hedgehog and ptc therapeutics can be used prophylatically in order to minimize ischemic damage which may result from an eventual stroke. A patient who is worsening under supervision requires more urgent management than one who has been stable for a week or more.

The subject method may also find particular utility in treating or preventing the adverse neurological consequences of surgery. For example, coronary bypass surgery requires the use of heart-lung machines, which tend to introduce air bubbles into the circulatory system that may lodge in the brain. The presence of such air bubbles robs neuronal tissue of oxygen, resulting in anoxia and ischemia. Pre- or post-surgical administration of the hedgehog and/or ptc therapeutics of the present invention will treat or prevent the resulting ischemia. In a preferred embodiment, the subject therapeutics are administered to patients undergoing cardiopulmonary bypass surgery or carotid endarterectomy surgery.

In still other embodiments, the subject method can be used in the prevention and/or treatment of hypoxia, e.g., as a neuroprotective agent. For instance, the subject method can be used prophylactically to lessen the neuronal cell death caused by altitude-induced hypoxia.

A method which is "neuroprotective", in the case of cerebral ischemia, results in diminished infarct volume relative to that which would occur in the absence of treatment with a hedgehog or ptc therapeutic. That is a neuroprotective therapy is intended to maintain or rescue damaged nerve cells, preventing their death.

The treatment methods of the present invention can be combined with the use of (a) anticoagulants, (b) antiplatelet agents, and/or (c) vascular surgery. Co-administered with suitable anti-coagulant agents, antiplatelet agents, thrombin inhibitors, and/or thrombolytic agents, may afford an efficacy advantage over any of the agents alone, and may do so while permitting the use of lower doses of each. A lower dosage minimizes the potential of side effects, thereby providing an increased margin of safety. The two (or more) agents are administered in combination according to the invention. The term "in combination" in this context means that the drugs are given substantially contemporaneously, either simultaneously or sequentially. If given sequentially, at the onset of administration of the second agent, the first of the two agents is preferably still detectable at effective concentrations at the site of treatment.

The term "anti-coagulant agents" (or coagulation inhibitory agents), as used herein, denotes agents that inhibit blood coagulation. Such agents include warfarin, heparin, or low molecular weight heparin (LMWH), including pharmaceutically acceptable salts or prodrugs thereof. For reasons of efficacy, the preferable anti-coagulant agents are warfarin or heparin or LMWH. The warfarin employed herein, may be, for example, crystalline warfarin or amorphous sodium warfarin. The heparin employed herein may be, for example, the sodium or sulfate salts thereof.

The term "anti-platelet agents" (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), which has been well researched and widely used with good results, and piroxicam, which exerts its anti-platelet effect when dosed once daily, are preferred compounds, especially aspirin. Piroxicam is commercially available from Pfizer Inc. (New York, N.Y.), as FELDANE TM. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase "thrombin inhibitors" (or anti-thrombin agents), as used herein, denotes inhibitors of the serine protease thrombin. By inhibiting thrombin, various thrombin mediated processes such as thrombin-mediated platelet activation (that is, for example, the aggregation of platelets, and/or the granular secretion of plasminogen activator inhibitor-1 and/or serotonin) and/or fibrin formation are disrupted. Such inhibitors include boropeptides, hirudin and argatroban, including pharmaceutically acceptable salts and prodrugs thereof. Preferably the thrombin inhibitors are boropeptides. By boropeptides, it is meant, N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The phrase "thrombolytic agents" or "fibrinolytic agents" or "thrombolytics" or "fibrinolytics", as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 0 28 489, the disclosures of which are hereby incorporated herein by reference herein, in their entirety. Anistreplase is commercially available from the Beecham Group, Middlesex, England, under the trademark EMINASE TM. The term urokinase, as used herein, is intended to denote both dual and single chain urokinase, the latter also being referred to herein as prourokinase.

In yet other embodiments, the subject method can be carried out conjointly with the administration of growth and/or trophic factors. For instance, the trophic growth factor basic FGF has been demonstrated in the art to be useful in the functional recovery following experimental stroke. In experiments providing exogenous administration of bFGF after infarction, the early administration of bFGF was found to reduce infarct size. See, for example, Kawamata et al. (1997) *Adv Neurol* 73: 377–82. Likewise, progesterone has been shown to be neuroprotective after transient middle cerebral artery occlusion in male rats. Jiang et al. (1996) *Brain Res* 735:101–7. Other agents with which the subject hedgehog and ptc therapeutics can be coadministered include nitro-L-arginine, transforming growth factor-β1 (TGF-beta 1) has been shown to rescue cultured neurons from excitotoxic and hypoxic cell death and to reduce infarct size after focal cerebral ischemia in mice and rabbits. In other instances, the combinatorial therapy can include a trophic factor such as nerve growth factor, cilliary neurotrophic growth factor, schwanoma-derived growth factor, glial growth factor, stiatal-derived neuronotrophic factor, platelet-derived growth factor, and scatter factor (HGF-SF). Antimitogenic agents can also be used, as for example, cytosine, arabinoside, 5-fluorouracil, hydroxyurea, and methotrexate.

Determination of a therapeutically effective amount and a prophylactically effective amount of a hedgehog or ptc therapeutic, e.g., to be adequately neuroprotective, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated, the risk of further ischemic or hypoxic damage to the CNS, and the particular agent being employed. In determining the therapeutically effective neuroprotective amount or dose, and the prophylactically effective amount or dose, a number of factors are considered by the attending clinician, including, but not limited to: the specific cause of the ischemic or hypoxic state and its likelihood of recurring or worsening; pharmacodynamic characteristics of the particular agent and its mode and route of administration; the desired time course of treatment; the species of mammal; its size, age, and general health; the response of the individual patient; the particular compound administered; the bioavailability characteristics of the preparation administered; the dose regimen selected; the kind of concurrent treatment (i.e., the interaction of the hedgehog or ptc therapeutic with other co-administered therapeutics); and other relevant circumstances.

Treatment can be initiated with smaller dosages which are less than the optimum dose of the agent. Thereafter, the dosage should be increased by small increments until the optimum effect under the circumstances is reached. For convenience, the total daily dosage may be divided and administered in portions during the day if desired. A therapeutically effective antineoplastic amount and a prophylactically effective neuroprotective amount of a hedgehog polypeptide, for instance, is expected to vary from concentrations about 0.1 nanogram per kilogram of body weight per day (kg/day) to about 100 kg/day.

Potential hedgehog and ptc therapeutics, such as described below, can be tested by measuring the volume of cerebral infarction in animals receiving systemic injections. For instance, selected agents can be evaluated in the focal stroke model involving permanent middle cerebral artery occlusion (MCAO) in the spontaneously hypertensive rat. This procedure results in a reliably large neocortical infarct volume that is measured by means of vital dye exclusion in serial slices through the brain 24 hours after MCAO. Tamura et al. (1981) *J Cerebral Blood Flow and Metabolism* 1:53–60.

The middle cerebral artery is the cerebral blood vessel most susceptible to stroke in humans. In animals, coagulation, permanent ligation or permanent placement of an occluding thread in the artery produces a permanent focal stroke affecting the MCA territory. Transient ligation or occlusion results in transient focal stroke. Both transient and permanent focal strokes result in varying degrees of edema and infarction in the affected brain regions. The ability of compounds to reduce the volumes of edema and infarction is considered a measure of their potential as anti-stroke treatment.

Compounds which are determined to be effective for the prevention or treatment of cerebral infarction and the like in animals, e.g., dogs, rodents, may also be useful in treatment of tumors in humans. Those skilled in the art of treating such disorders in humans will be guided, from the data obtained in animal studies, to the correct dosage and route of administration of the compound to humans. In general, the determination of dosage and route of administration in humans is expected to be similar to that used to determine administration in animals.

The identification of those patients who are in need of prophylactic treatment for ischemic or hypoxic states is well within the ability and knowledge of one skilled in the art. Certain of the methods for identification of patients which are at risk of cerebral infarction which can be treated by the subject method are appreciated in the medical arts, such as family history of the development of a particular disease state and the presence of risk factors associated with the development of that disease state in the subject patient. A clinician skilled in the art can readily identify such candidate patients, by the use of, for example, clinical tests, physical examination and medical/family history.

IV. Exemplary Hedgehog Therapeutic Compounds

The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject therapeutics can be derived are characterized by a signal peptide, a highly conserved N-terminal region, and a more divergent C-terminal domain. In addition to signal sequence cleavage in the secretory pathway (Lee, J. J. et al. (1992) *Cell* 71:33–50; Tabata, T. et al. (1992) *Genes Dev.* 2635–2645; Chang, D. E. et al. (1994) *Development* 120:3339–3353), hedgehog precursor proteins naturally undergo an internal autoproteolytic cleavage which depends on conserved sequences in the C-terminal portion (Lee et al. (1994) *Science* 266:1528–1537; Porter et al. (1995) *Nature* 374:363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) *Mol. Cell Biol.* 15:2294–2303; Porter et al. (1995) supra; Ekker, S. C. et al. (1995) *Curr. Biol.* 5:944–955; Lai, C. J. et al. (1995) *Development* 121:2349–2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al. (1995) *Development* 121:2537–2547; Roelink, H. et al. (1995) *Cell* 81:445–455). Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J. A. et al. (1996) *Cell* 86, 21–34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single drosophila hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; and a zebrafish Thh is encoded by SEQ ID No. 8.

TABLE 1

| Guide to hedgehog sequences in Sequence Listing | | |
|---|---|---|
| | Nucleotide | Amino Acid |
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Zebrafish Thh | SEQ ID No. 8 | SEQ ID No. 17 |
| Drosophila HH | SEQ ID No. 9 | SEQ ID No. 18 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein. In addition to proteolytic fragmentation, the vertebrate hedgehog proteins can also be modified post-translationally, such as by glycosylation and/or addition of cholesterol, though bacterially produced (e.g., unglycosylated/uncholesterolized) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, the hedgehog therapeutic is a polypeptide encodable by a nucleotide sequence that hybridizes under stringent conditions to a hedgehog coding sequence represented in one or more of SEQ ID Nos:1–9. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques well known in the art. For example, a cDNA encoding a hedgehog protein can be obtained by isolating total mRNA from a cell, e.g., a mammalian cell, e.g., a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Preferred nucleic acids encode a hedgehog polypeptide comprising an amino acid sequence at least 60% homologous, more preferably 70% homologous and most preferably 80% homologous with an amino acid sequence selected from the group consisting of SEQ ID Nos: 10–18. Nucleic acids which encode polypeptides at least about 90%, more preferably at least about 95%, and most preferably at least about 98–99% homology with an amino acid sequence represented in one of SEQ ID Nos: 10–18 are also within the scope of the invention.

Hedgehog polypeptides preferred by the present invention, in addition to native hedgehog proteins, are at least 60% homologous, more preferably 70% homologous and most preferably 80% homologous with an amino acid sequence represented by any of SEQ ID Nos:10–18. Polypeptides which are at least 90%, more preferably at least 95%, and most preferably at least about 98–99% homologous with a sequence selected from the group consisting of SEQ ID Nos: 10–18 are also within the scope of the invention. The only prerequisite is that the hedgehog polypeptide is capable of protecting neuronal cells against ischemic damage.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID Nos: 1–9 or 19.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1) and pBlueBac-derived vectors (such as the β-gal containing pBlueBac III).

When it is desirable to express only a portion of a hedgehog protein, such as a form lacking a portion of the N-terminus, i.e., a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g., of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenyl, myristyl, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30–3; and Kornblihtt et al. (1985) *EMBO* 4:1755–9) can be added to the hedgehog polypeptide to support attachment of the chimeric molecule to a cell through binding ECM components (Ruoslahti et al. (1987) *Science* 238:491–497; Pierschbacher et al. (1987) *J. Biol. Chem.* 262:17294–8.; Hynes (1987) *Cell* 48:549–54; and Hynes (1992) *Cell* 69:11–25).

In a preferred embodiment, the hedgehog polypeptide is isolated from, or is otherwise substantially free of, other cellular proteins, especially other extracellular or cell surface associated proteins which may normally be associated with the hedgehog polypeptide. The term "substantially free of other cellular or extracellular proteins" (also referred to herein as "contaminating proteins") or "substantially pure or purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos:10–18, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioctive fragments of hedgehog polypeptide, preferred hedgehog therapeutics include at least 50 amino acid residues of a hedgehog polypeptide, more preferably at least 100, and even more preferably at least 150.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24–197 of SEQ ID No. 15 and 28–202 of SEQ ID No. 16. By "corresponding approximately" it is meant that the sequence of interest is at most 20 amino acid residues different in length to the reference sequence, though more preferably at most 5, 10 or 15 amino acid different in length.

Still other preferred hedgehog polypeptides include an amino acid sequence represented by the formula A-B wherein: (i) A represents all or the portion of the amino acid sequence designated by residues 1–168 of SEQ ID No: 19; and B represents at least one amino acid residue of the amino acid sequence designated by residues 169–221 of SEQ ID No:19; (ii) A represents all or the portion of the amino acid sequence designated by residues 24–193 of SEQ ID No:15; and B represents at least one amino acid residue of the amino acid sequence designated by residues 194–250 of SEQ ID No:15; (iii) A represents all or the portion of the amino acid sequence designated by residues 25–193 of SEQ ID No:13; and B represents at least one amino acid residue of the amino acid sequence designated by residues 194–250 of SEQ ID No:13; (iv) A represents all or the portion of the amino acid sequence designated by residues 23–193 of SEQ ID No:11; and B represents at least one amino acid residue of the amino acid sequence designated by residues 194–250 of SEQ ID No:11; (v) A represents all or the portion of the amino acid sequence designated by residues 28–197 of SEQ ID No:12; and B represents at least one amino acid residue of the amino acid sequence designated by residues 198–250 of SEQ ID No:12; or (vi) A represents all or the portion of the amino acid sequence designated by residues 29–197 of SEQ ID No:16; and B represents at least one amino acid residue of the amino acid sequence designated by residues 198–250 of SEQ ID No:16. In certain preferred embodiments, A and B together represent a contiguous polypeptide sequence of the designated sequence, A represents at least 25, 50, 75, 100, 125 or 150 amino acids of the designated sequence, and B represents at least 5, 10, or 20 amino acid residues of the amino acid sequence designated by corresponding entry in the sequence listing, and A and B together preferably represent a contiguous sequence corresponding to the sequence listing entry. Similar fragments from other hedgehog proteins are also contemplated, e.g., fragments which correspond to the preferred fragments from the sequence listing entries which are enumerated above.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as agonists of a wild-type (e.g., "authentic") hedgehog protein. For example, Roman et al. (1994) *Eur J Biochem* 222:65–73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack glycosylation sites (e.g., to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that certain isolated replacements of amino acids, e.g., replacement of an amino acid residue with another related amino acid (i.e., isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic= lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W H Freeman and Co.: 1981). Whether a change in the amino acid sequence of a peptide results in a functional hedgehog homolog (e.g., functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried out using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g., homologs) that are functional in binding to a receptor for hedgehog proteins. The purpose of screening such combinatorial libraries is to generate, for example, novel hedgehog homologs which can act as neuroprotective agents. To illustrate, hedgehog homologs can be engineered by the present method to provide more efficient binding to a cognate receptor, such as patched, retaining neuroprotective activity. Thus, combinatorially-derived homologs can be generated to have an increased potency relative to a naturally occurring form of the protein. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al. state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8:309–314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g., for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g., the N-terminal approximately 221 residues of the mature protein) of each of the Shh clones produces a degenerate set of Shh polypeptides represented by the general formula:

C-G-P-G-R-G-X(1)-G-X(2)-R-R-H-P-K-K-L-T-P-L-A-Y-K-Q-F-I-P-N-V-A-E-

K-T-L-G-A-S-G-R-Y-E-G-K-I-X(3)-R-N-S-E-R-F-K-E-L-T-P-N-Y-N-P-D-I-I-F-

K-D-E-E-N-T-G-A-D-R-L-M-T-Q-R-C-K-D-K-L-N-X(4)-L-A-I-S-V-M-N-X(5)-

W-P-G-V-X(6)-L-R-V-T-E-G-W-D-E-D-G-H-H-X(7)-E-E-S-L-H-Y-E-G-R-A-

V-D-I-T-T-S-D-R-D-X(8)-S-K-Y-G-X(9)-L-X(10)-R-L-A-V-E-A-G-F-D-W-V-

Y-Y-E-S-K-A-H-I-H-C-S-V-K-A-E-N-S-V-A-A-K-S-G-G-C-F-P-G-S-A-X(11)-

V-X(12)-L-X(13)-X(14)-G-G-X(15)-K-X-(16)-V-K-D-L-X(17)-P-G-D-X(18)-V-

L-A-A-D-X(19)-X(20)-G-X(21)-L-X(22)-X(23)-S-D-F-X(24)-X(25)-F-X(26)-D-

R (SEQ ID No: 19), wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp ; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gln; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gln, Asn, Glu, or Asp; Xaa(14) represents His, Phe, Tyr, Thr, Gln, Asn, Glu or Asp; Xaa(15) represents Gln, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gln, Ser, Thr or Cys; Xaa(18) represents Arg, Lys, Met or Ile; Xaa(19) represents Ala, Gly, Cys, Asp, Glu, Gln, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gln; Xaa(22)

represent Leu, Val, Met or Ile; Xaa(23) represents Phe, Tyr, Thr, His or Trp; Xaa(24) represents Ile, Val, Leu or Met; Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

C-G-P-G-R-G-X(1)-X(2)-X(3)-R-R-X(4)-X(5)-X(6)-P-K-X(7)-L-X(8)-P-L-X(9)-

Y-K-Q-F-X(10)-P-X(11)-X(12)-X(13)-E-X(14)-T-L-G-A-S-G-X(15)-X(16)-E-G-

X(17)-X(18)-X(19)-R-X(20)-S-E-R-F-X(21)-X(22)-L-T-P-N-Y-N-P-D-I-I-F-K-

D-E-E-N-X(23)-G-A-D-R-L-M-T-X(24)-R-C-K-X(25)-X(26)-X(27)-N-X(28)-L-

A-I-S-V-M-N-X(29)-W-P-G-V-X(30)-L-R-V-T-E-G-X(31)-D-E-D-G-H-H-

X(32)-X(33)-X(34)-S-L-H-Y-E-G-R-A-X(35)-D-I-T-T-S-D-R-D-X(36)-X(37)-K-

Y-G-X(38)-L-X(39)-R-L-A-V-E-A-G-F-D-W-V-Y-Y-E-S-X(40)-X(41)-H-X(42)-

H-X(43)-S-V-K-X(44)-X(45)    (SEQIDNo:20), wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g., the polypeptides of the library all include a signal sequence but no transmembrane or cytoplasmic domains), and is used to transfect a eukaryotic cell that can be co-cultured with neuronal cells. A functional hedgehog protein secreted by the cells expressing the combinatorial library will diffuse to neighboring neuronal cells and induce a particular biological response, such as protection against cell death under oxygen-deprevation conditions (e.g., high $CO_2$ culture conditions). The pattern of detection of proliferation will resemble a gradient function, and will allow the isolation (generally after several repetitive rounds of selection) of cells producing hedgehog homologs active as neuroprotective agents with respect to neuronal cells.

To illustrate, target neuronal cells are cultured in 24-well microtitre plates. Other eukaryotic cells are transfected with the combinatorial hedgehog gene library and cultured in cell culture inserts (e.g., Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as neuroprotection, the inserts are removed and the effect of the variant hedgehog proteins on the target cells determined. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical E.coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffths et al. (1993) EMBO J 12:725–734; Clackson et al. (1991) Nature 352:624–628; and Barbas et al. (1992) PNAS 89:4457–4461).

In an illustrative embodiment, the recombinant phage antibody system (RPAS, Pharamacia Catalog number 27-9400-01) can be easily modified for use in expressing and screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the hedgehog protein to generate mimetics, e.g., peptide or non-peptide agents, which are able to mimic the neuroprotective activity of a naturally-occurring hedgehog polypeptide. Thus, such mutagenic techniques as described above are also useful to map the determinants of the hedgehog proteins which participate in protein-protein interactions involved in, for example, binding of the subject hedgehog polypeptide to other extracellular matrix components such as its receptor (s). To illustrate, the critical residues of a subject hedgehog polypeptide which are involved in molecular recognition of an hedgehog receptor such as patched can be determined and used to generate hedgehog-derived peptidomimetics which competitively bind with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. After distinguishing between agonist and antagonists, such agonistic mimetics may be used to mimic the normal function of a hedgehog protein in the treatment ischemia. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res. Commun126:419; and Dann et al. (1986) Biochem Biophys Res Commun 134:71).

Recombinantly produced forms of the hedgehog proteins can be produced using, e.g, expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either a neuroprotective form of a hedgehog polypeptide. Thus, another aspect of the invention features expression vectors for in vivo transfection of a hedgehog polypeptide in particular cell types so as to cause ectopic expression of a hedgehog polypeptide in neuronal tissue.

Formulations of such expression constructs may be administered in any biologically effective carrier, e.g., any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g., locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g., a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology* Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including neuronal cells, in vitro and/or in vivo (see, for example, Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992)

J. Gen Virol 73:3251–3255; and Goud et al. (1983) Virology 163:251–254); or coupling cell surface receptor ligands to the viral env proteins (Neda et al. (1991) J Biol Chem 266:14143–14146). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector into an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including neuronal cells (Rosenfeld et al. (1992) cited supra).

Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). A hedgehog expression construct can be delivered in a gene therapy construct to dermal cells by, e.g., electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral vectors, the pharmaceutical preparation can comprise one or more cells which produce the gene delivery system.

In yet another embodiment, the hedgehog or ptc therapeutic can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes constitutive expression of the hedgehog gene or which causes inducible expression of the gene under conditions different from the normal expression pattern of the gene. Other genes in the patched signaling pathway can be similarly targeted. A variety of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.) which direct recombination and (2) heterologous transcriptional regulatory sequence(s) which is to be operably linked to the coding sequence for the genomic hedgehog gene upon recombination of the gene activation construct. For use in generating cultures of hedgehog producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of an activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regulatory elements, locus control regions, transcription factor binding sites, or combinations thereof Promoters/enhancers which may be used to control the expression of the targeted gene in vivo include, but are not limited to, the cytomegalovirus (CMV) promoter/enhancer (Karasuyama et al., 1989, J. Exp. Med., 169:13), the human β-actin promoter (Gunning et al. (1987) PNAS 84:4831–4835), the glucocorticoid-inducible promoter present in the mouse mammary tumor virus long terminal repeat (MMTV LTR) (Klessig et al. (1984) Mol. Cell Biol. 4:1354–1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bernoist et al. (1981) Nature 290:304–310; Templeton et al. (1984) Mol. Cell Biol., 4:817; and Sprague et al. (1983) J. Virol., 45:773), the promoter contained in the 3' long terminal repeat of Rous sarcoma virus (RSV) (Yamanoto et al., 1980, Cell, 22:787–797), the herpes simplex virus (HSV) thymidine kinase promoter/enhancer (Wagner et al. (1981) PNAS 82:3567–71), and the herpes simplex virus LAT promoter (Wolfe et al. (1992) Nature Genetics, 1:379–384).

In an exemplary embodiment, portions of the 5' flanking region of the human Shh gene are amplified using primers which add restriction sites, to generate the following fragments 5'-GCGCGCTTCGAAGCGAGGCAGCCAGC-
    GAGGGAGAGAGCGAGCGGGCGAGCCGGAGCGAGGAA
    ATCGATGCGCGC (primer 1)         (SEQ ID NO: 21)

5'-gcgcgcagatctGGGAAAGCGCAA-
    GAGAGAGCGCACACGCACACACCCGC-
    CGCGCGCACTCG GGATCCGC
    GCGC (primer 2)         (SEQ ID NO: 22)

As illustrated, primer 1 includes a 5' non-coding region of the human Shh gene and is flanked by an AsuII and ClaI restriction sites. Primer 2 includes a portion of the 5' non-coding region immediately 3' to that present in primer 1. The hedgehog gene sequence is flanked by XhoII and BamHI restriction sites. The purified amplimers are cut with each of the enzymes as appropriate.

The vector pCDNA1.1 (Invitrogen) includes a CMV promoter. The plasmid is cut with with AsuII, which cleaves just 3' to the CMV promoter sequence. The AsuII/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, and cut with AsuII and BamHI to produce the gene activation construct:

CGAAGCGAGGCAGCCAGEGAGG-
        GAGAGAGCGAGCGGGCGAGCCGGAGC-
        GAGGGAAATCGAAGGTT

CGAATCCTTCCCCCACCACCAT-
        CACTTTCAAAAGTCCGAAAGAATCT-
        GCTCCCTGCTTGTGTGT

TGGAGGTCGCTGAGTAGTGCGCGAG-
        TAAAATTTAAGCTACAACAAGGCAAG-
        GCTTGACCGACAA

TTGCATGAAGAATCTGCTTAGGGTTAG-
        GCGTTTTGCGCTGCTTCGCGATGTACGGGCCAGATAT

ACGCGTTGACATTGATTATTGACTAGT-
        TATTAATAGTAATCAATTACGGGGTCATTAGTTCATA

GCCCATATATGGAGTTCCGCGTTACAT-
        AACTTACGGTAAATGGCCCGCCTGGCTGACCGCCCAA

CGACCCCCGCCCATTGACGTCAATAAT-
        GACGTATGTTCCCATAGTAACGCCAATAGGGACTTTC

CATTGACGTCAATGGGTGGACTATT-
        TACGGTAAACTGCCCACTTGGCAGTACATCAAGTGTATC

ATATGCCAAGTACGCCCCCTATTGACGT-
        CAATGACGGTAAATGGCCCGCCTGGCATTATGCCCA

GTACATGACCTTATGGGACTTTCCTACT-
        TGGCAGTACATCTACGTATTAGTCATCGCTATTACC

ATGGTGATGCGGTTTTGGCAGTACAT-
        CAATGGGCGTGGATAGCGGTTTGACTCACGGGGATTTC

CAAGTCTCCACCCCATTGACGTCAATGG-
        GAGTTTGTTTTGGCACCAAAATCAACGGGACTTTCC

AAAATGTCGTAACAACTCCGCCCCAT-
        TGACGCAAATGGGCGGTAGGCGTGTACGGTGGGAGGTC

TATATAAGCAGAGCTCTCTGGCTAACTA-
        GAGAACCCACTGCTTACTGGCTTATCGAAATTAATA

CGACTCACTATAGGGAGACCCAAGCTTG-
        GTACCGAGCTCGGATC GATCTGGGAAAGCGCAAGAG

AGAGCGCACACGCACACACCCGCCGCG
        CGCACTCGG         (SEQ ID NO: 23)

In this construct, the flanking primer 1 and primer 2 sequences provide the recombination region which permits the insertion of the CMV promoter in front of the coding sequence for the human Shh gene. Other heterologous promoters (or other transcriptional regulatory sequences) can be inserted in a genomic hedgehog gene by a similar method.

In still other embodiments, the replacement region merely deletes a negative transcriptional control element of the native gene, e.g., to activate expression, or ablates a positive control element, e.g., to inhibit expression of the targeted gene.

V. Exemplary ptc Therapeutic Compounds

In another embodiment, the subject method is carried out using a ptc therapeutic composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly in their role in the pathogenesis of neuronal cell death. In one embodiment, the assay evaluates the ability of a compound to modulate binding between a hedgehog polypeptide and a hedgehog receptor such as patched. In other embodiments, the assay merely scores for the ability of a test compound to alter the signal transduction activity of the patched protein. In this manner, a variety of hedgehog and/or ptc therapeutics, which will include ones with neuroprotective activity, can be identified. A variety of assay formats will suffice and, in light of the present disclosure, will be comprehended by a skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Accordingly, in an exemplary screening assay for ptc therapeutics, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

Agonist and antagonists of neuroprotection can be distinguished, and the efficacy of the compound can be assessed, by subsequent testing with neuronal cells.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see Genbank Accession numbers U40074 for chicken patched and U46155 for mouse patched), as well as from drosophila (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g., corresponding to residues Asn120-Ser438 and/or Arg770-Trp1027 of the human patched protein). For instance, the patched protein can be provided in soluble form, as for example a preparation of one of the extracellular domains, or a preparation of both of the extracellular domains which are covalently connected by an unstructured linker (see, for example, Huston et al. (1988) PNAS 85:4879; and U.S. Pat. No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cells by standard recombinant DNA techniques. These recombinant cells can be used for receptor binding, signal transduction or gene expression assays. Marigo et al. (1996) *Development* 122:1225–1233 illustrates a binding assay of human hedgehog to chick patched protein ectopically expressed in *Xenopus laevis* oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide; e.g., an $^{35}$S-labeled hedgehog polypeptide, and the test compound and incubated under conditions conducive to complex formation, e.g., at physiological conditions for salt and pH, though slightly more stringent conditions may be desired. Following incubation, the beads are washed to remove any unbound hedgehog polypeptide, and the matrix bead-bound radiolabel determined directly (e.g., beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g., paranitrophenylphosphate. Likewise, a fusion protein comprising the hedgehog polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g., from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g., phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374).

In addition to cell-free assays, such as described above, the readily available source of hedgehog proteins provided by the art also facilitates the generation of cell-based assays for identifying small molecule agonists of the neuroprotective activity of wild-type hedgehog proteins. Analogous to the cell-based assays described above for screening combinatorial libraries, neuronal cells which are sensitive to hedgehog-dependent protection against ischemic damage can be contacted with a hedgehog protein and a test agent of interest, with the assay scoring for anything from simple binding to the cell to modulation in hedgehog inductive responses by the target cell in the presence and absence of the test agent. As with the cell-free assays, agents which produce a statistically significant change in hedgehog activities (either inhibition or potentiation) can be identified.

In addition to characterizing cells that naturally express the patched protein, cells which have been genetically engineered to ectopically express patched can be utilized for drug screening assays. As an example, cells which either express low levels or lack expression of the patched protein, e.g., *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or anatagonists of hedgehog binding. Binding assays can be performed using whole cells. Furthermore, the recombinant cells of the present invention can be engineered to include other heterologous genes encoding proteins involved in hedgehog-dependent signal pathways. For example, the gene products of one or more of smoothened, costal-2 and/or fused can be co-expressed with patched in the reagent cell, with assays being sensitive to the functional reconstituion of the hedgehog signal transduction cascade.

Alternatively, liposomal preparations using reconstituted patched protein can be utilized. Patched protein purified from detergent extracts from both authentic and recombinant origins can be reconstituted in artificial lipid vesicles (e.g., phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists of hedgehog or patched activities. By detecting changes in intracellular signals, such as alterations in second messengers or gene expression in patched-expressing cells contacted with a test agent, candidate antagonists to patched signaling can be identified (e.g., having a hedgehog-like activity).

A number of gene products have been implicated in patched-mediated signal transduction, including patched, the transcription factor cubitus interruptus (ci), the serine/threonine kinase fused (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 *Development* 110, 291–301; Marigo et al., 1996 ) and the vertebrate homologs of the drosophila cubitus interruptus gene, the GLI genes (Hui et al. (1994) *Dev Biol* 162:402–413). Patched gene expression has been shown to be induced in cells of the limb bud and the neural plate that are responsive to Shh. (Marigo et al. (1996) *PNAS, in press; Marigo et al. (1996) Development* 122:1225–1233). The GLI genes encode putative transcription factors having zinc finger DNA binding domains (Orenic et al. (1990) *Genes &*

Dev 4:1053–1067; Kinzler et al. (1990) *Mol Cell Biol* 10:634–642). Transcription of the GLI gene has been reported to be upregulated in response to hedgehog in limb buds, while transcription of the GLI3 gene is downregulated in response to hedgehog induction (Marigo et al. (1996) *Development* 122:1225–1233). By selecting transcriptional regulatory sequences from such target genes, e.g., from patched or GLI genes, that are responsible for the up- or down-regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as antagonists of ptc, e.g., which may be useful as neuroprotective agents.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270:10314–10322; and Kube et al. (1995) *Cytokine* 7:1–7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsive to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular stimulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) *Genes & Dev* 10:647). High PKA activity has been shown to antagonize hedgehog signaling in these systems. Conversely, inhibitors of PKA will mimic and/or potentiate the action of hedgehog. Although it is unclear whether PKA acts directly downstream or in parallel with hedgehog signaling, it is possible that hedgehog signalling occurs via inhibition of PKA activity. Thus, detection of PKA activity provides a potential readout for the instant assays. In certain embodiments, a preferred ptc therapeutic inhibits PKA with a $K_i$ less than 10 nM, preferably less than 1 nM, even more preferably less than 0.1 nM.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

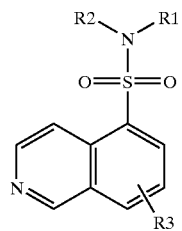

wherein,

- $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH; —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$, or
- $R_1$ and $R_2$ taken together with N form a heterocycle (substituted or unsubstituted);
- $R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O —$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$;
- $R_8$ represents a substituted or unsubstituted aryl, aralkyl, cycloalkyl, cycloalkenyl, or heterocycle; and
- n and m are independently for each occurrence zero or an integer in the range of 1 to 6.

In a preferred embodiment, the PKA inhibitor is N-[2-((p-bromocinnamyl)amino)ethyl]-5-isoquinolinesulfonamide (H-89; Calbiochem Cat. No. 371963), e.g., having the formula:

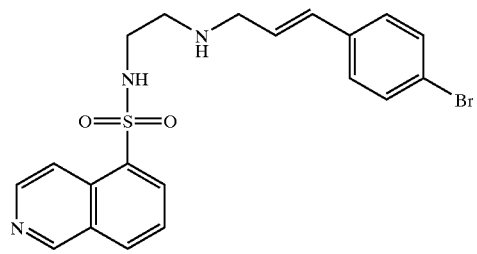

In another embodiment, the PKA inhibitor is 1-(5-isoquinolinesulfonyl)-2-methylpiperazine (H-7; Calbiochem Cat. No. 371955), e.g., having the formula:

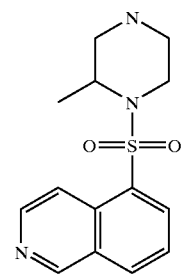

In still other embodiments, the PKA inhibitor is KT5720 (Calbiochem Cat. No. 420315), having the structure

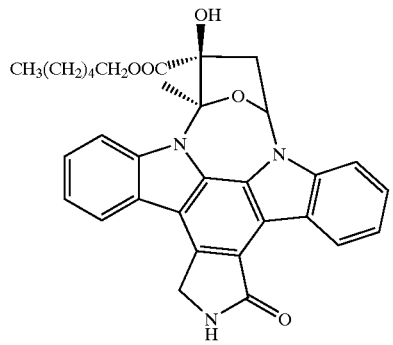

The hedgehog pathway can be agonized by antagonizing the cAMP pathway, e.g., by using an agonist of cAMP phosphodiesterase, or by using an antagonist of adenylate cyclase, cAMP or protein kinase A (PKA). Compounds which may reduce the levels or activity of cAMP include prostaglandylinositol cyclic phosphate (cyclic PIP), endothelins (ET)-1 and -3, norepinepurine, K252a, dideoxyadenosine, dynorphins, melatonin, pertussis toxin, staurosporine, $G_i$ agonists, MDL 12330A, SQ 22536, GDPssS and clonidine, beta-blockers, and ligands of G-protein coupled receptors. Additional compounds are disclosed in U.S. Pat. Nos. 5,891,875, 5,260,210, and 5,795,756.

Exemplary peptidyl inhibitors of PKA activity include the PKA Heat Stable Inhibitor (isoform α; see, for example, Calbiochem Cat. No. 539488, and Wen et al. (1995) *J Biol Chem* 270:2041).

In certain embodiments, a compound which is an agonist or antagonist of PKA is chosen to be selective for PKA over other protein kinases, such as PKC, e.g., the compound modulates the activity of PKA at least an order of magnitude more strongly than it modulates the activity of another protein kinase, preferably at least two orders of magnitude more strongly, even more preferably at least three orders of magnitude more strongly. Thus, for example, a preferred inhibitor of PKA may inhibit PKA activity with a $K_i$ at least an order of magnitude lower than its $K_i$ for inhibition of PKC, preferably at least two orders of magnitude lower, even more preferably at least three orders of magnitude lower. In certain embodiments, a ptc therapeutic inhibits PKC with a $K_i$ greater than 1 μM, greater than 100 nM, preferably greater than 10 nM.

Certain hedgehog receptors may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45–56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the drosophila gene fused (fu) which encodes a serine/threonine kinase has been identified as a potential downstream target in hedgehog signaling. (Preat et al., 1990 *Nature* 347, 87–89; Therond et al. 1993, *Mech Dev.* 44. 65–80). The ability of compounds to modulate serine/threonine kinase activation could be screened using colony immunoblotting (Lyons and Nelson (1984) *Proc. Natl. Acad. Sci. USA* 81:7426–7430) using antibodies against phosphorylated serine or threonine residues. Reagents for performing such assays are commercially available, for example, phosphoserine and phosphothreonine specific antibodies which measure increases in phosphorylation of those residues can be purchased from commercial sources.

In yet another embodiment, the ptc therapeutic is an antisense molecule which inhibits expression of a protein involved in a patched-mediated signal transduction pathway. To illustrate, by inhibiting the expression of a protein involved in patched signals, such as fused, costal-2, smoothened and/or Gli genes, or patched itself, the ability of the patched signal pathway(s) to alter the ability of a cell to withstand ischemic conditions can be altered, e.g., potentiated or repressed.

As used herein, "antisense" therapy refers to administration or in situ generation of oligonucleotide probes or their derivatives which specifically hybridize (e.g., bind) under cellular conditions with cellular mRNA and/or genomic DNA encoding a hedgehog protein, patched, or a protein involved in patched-mediated signal transduction. The hybridization should inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g., exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc therapeutic can be an antisense construct for inhibiting the expression of patched, e.g., to mimic the inhibition of patched by hedgehog. Exemplary antisense constructs include:

| | |
|---|---|
| 5'-GTCCTGGCGCCGCCGCCGCCGTCGCC | (SEQ ID NO: 24) |
| 5'-TTCCGATGACCGGCCTTTCGCGGTGA | (SEQ ID NO: 25) |
| 5'-GTGCACGGAAAGGTGCAGGCCACACT | (SEQ ID NO: 26) |

VI. Exemplary Pharmaceutical Preparations of Hedgehog and ptc Therapeutics

The source of the hedgehog and ptc therapeutics to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, infer alia, from PCT publications WO 95/18856 and WO 96/17924.

Those of skill in treating neural tissues can determine the effective amount of an hedgehog or ptc therapeutic to be formulated in a pharmaceutical or cosmetic preparation.

The hedgehog or ptc therapeutic formulations used in the method of the invention are most preferably applied in the form of appropriate compositions. As appropriate compositions there may be cited all compositions usually employed for systemically or locally (such as intrathecal) administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular hedgehog or ptc therapeutic as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

It is especially advantageous to formulate the subject compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications which can be considered cosmetic uses. Cosmetic compositions known in the art, preferably hypoallergic and pH controlled are especially preferred, and include toilet waters, packs, lotions, skin milks or milky lotions. The preparations contain, besides the hedgehog or ptc therapeutic, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g., antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g., the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the hedgehog or ptc therapeutic, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage.

Particular compositions for use in the method of the present invention are those wherein the hedgehog or ptc therapeutic is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of hedgehog or ptc therapeutic, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc therapeutics is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated hedgehog or ptc therapeutic can be employed directly or they can be employed in a suitable pharmaceutically acceptable carrier for localized administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes. buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanolamine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an hh at a particular target site. Such embodiments of the present invention can be used for the delivery of an exogenously purified hedgehog protein, which has been incorporated in the polymeric device, or for the delivery of hedgehog produced by a cell encapsulated in the polymeric device.

An essential feature of certain embodiments of the implant can be the linear release of the therapeutic, which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials,* ed. by David Williams (MIT Press: Cambridge, Mass., 1990); and the Sabel et al. U.S. Pat. No. 4,883,666.

In another embodiment of an implant, a source of cells producing the therapeutic, e.g., secreting a soluble form of a hedgehog protein, is encapsulated in implantable hollow fibers or the like. Such fibers can be pre-spun and subsequently loaded with the cell source (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the cells (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotehnol. Bioeng.* 29:1135–1143; and Aebischer et al. (1991) *Biomaterials* 12:50–55).

Exemplification

The invention now being generally described, it will be more readily understood by reference to the following examples which are included merely for purposes of illustration of certain aspects and embodiments of the present invention, and are not intended to limit the invention.

Sonic Hedgehog (Shh) was evaluated in the focal stroke model involving permanent middle cerebral artery occlusion (MCAO) in the spontaneously hypertensive rat. Samples of the proteins were tested as a neuroprotective agent by measuring the volume of cerebral infarction, by means of vital dye exclusion, in animals receiving systemic injections. For review of the MCAO, see Tamura et al. (1981) *J Cerebral Blood Flow and Metabolism* 1:53–60.

Briefly, male Wistar rats, weighing about 270–300 g were treated systemically with Shh at 500 $\mu$g/kg/hr for 3 hrs at 0.5 ml/hr. Control animals received buffer at same dilution as Shh stock for the same period of time and volumes.

Prior to administration of the Shh or control stocks, the MCAO animals were generated as follows: the rats were anesthesized, with 400 mg/ml chloral hydrate, and their femoral vein and artery were cannulated. Mean arterial blood pressure was monitered and blood samples taken for blood gas measurements. A half-hour later, the middle cereberal artery was occluded with a nylon monofilament suture inserted via carotid artery. Half-hour after onset of occlusion, having allowed animal to awake, infusion of Shh or buffer/vehicle was started. The catheters were removed, and the animals were returned to their cages. At 24 hours post-surgery, the animals sacrificed by decapitation. Their brains were removed and cut into 2 mm serial, coronal sections. The sections stained with TTC stain and then fixed in neutral buffered formalin. Infarct volumes measured by quantitative morphometry and expressed as a percentage of the total hemispheric volume (normalized against the contralateral hemisphere to correct for edema-associated swelling).

FIG. 1 illustrates the results of the above-referenced experiments. A substantial decrease in the volume of the cerebral infarct was observed in the hedgehog treated rats relative to the control rats. While not shown in FIG. 1, its was further observed that there was no statistically significant effect of hedgehog on blood pressure, pH, $O_2$, or $pCO_2$.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for the treatment of cerebral ischemia which comprises systemically administering to a patient in need thereof a hedgehog polypeptide in an amount effective to reduce cerebral ischemia, wherein said hedgehog polypeptide comprises an amino acid sequence that (a) binds to a naturally occurring patched receptor and promotes hedgehog signal transduction, and (b) is encodable by a nucleic acid sequence designated in SEQ ID NO: 4, SEQ ID NO: 6, or an N-terminal auto-proteolytic fragment thereof.

2. The method of claim 1, wherein the patient is treated prophylactically.

3. The method of claim 1, further comprising administering one or more of an anticoagulant, an antiplatelet agent, a thrombin inhibitor, and/or a thrombolytic agent.

4. The method of claim 1, further comprising performing vascular surgery.

5. The method of claim 4, wherein the vascular surgery comprises carotid endarterectomy.

6. A method for the treatment of cerebral ischemia which comprises systemically administering to a patient in need thereof a hedgehog polypeptide in an amount effective to reduce cerebral ischemia, wherein said hedgehog polypeptide comprises an amino acid sequence that (a) binds to a naturally occurring patched receptor and promotes hedgehog signal transduction, and (b) is identical to SEQ ID NO: 13, SEQ ID NO: 15, or an N-terminal auto-proteolytic fragment thereof.

7. A method for the treatment of cerebral ischemia which comprises systemically administering to a patient in need thereof a hedgehog polypeptide and at least one additional agent, in an amount effective to reduce cerebral ischemia, wherein said hedgehog polypeptide comprises an amino acid sequence that (a) binds to a naturally occurring patched receptor and promotes hedgehog signal transduction, and (b) is identical to SEQ ID NO: 13, SEQ ID NO: 15, or an N-terminal auto-proteolytic fragment thereof, and wherein said additional agent is selected from at least one of an anticoagulant, an antiplatlet agent, a thrombin inhibitor, or a thrombolytic agent.

8. A method for the treatment of cerebral ischemia which comprises systemically administering to a patient in need thereof a hedgehog polypeptide in an amount effective to reduce cerebral ischemia, wherein said hedgehog polypeptide comprises an amino acid sequence that (a) binds to a naturally occurring patched receptor and promotes hedgehog signal transduction, and (b) is identical to SEQ ID NO: 13, SEQ ID NO: 15, or an N-terminal auto-proteolytic fragment thereof, and wherein said method additionally includes surgery.

* * * * *